United States Patent
Banister et al.

(10) Patent No.: US 9,238,102 B2
(45) Date of Patent: Jan. 19, 2016

(54) LOW PROFILE ACTUATOR AND IMPROVED METHOD OF CAREGIVER CONTROLLED ADMINISTRATION OF THERAPEUTICS

(75) Inventors: Mark Banister, Tucson, AZ (US); William G. Bloom, Encinitas, CA (US); Yordan M. Geronov, Tucson, AZ (US); Mark D. McWilliams, San Diego, CA (US); David Swenson, Tucson, AZ (US); Mark A. Van Veen, Cardiff by the Sea, AZ (US)

(73) Assignee: MEDIPACS, INC., San Diego, CA (US)

( * ) Notice: Subject to any disclaimer, the term of this patent is extended or adjusted under 35 U.S.C. 154(b) by 526 days.

(21) Appl. No.: 13/395,627

(22) PCT Filed: Sep. 10, 2010

(86) PCT No.: PCT/US2010/048489
§ 371 (c)(1),
(2), (4) Date: Mar. 12, 2012

(87) PCT Pub. No.: WO2011/032011
PCT Pub. Date: Mar. 17, 2011

(65) Prior Publication Data
US 2012/0191060 A1  Jul. 26, 2012

Related U.S. Application Data

(60) Provisional application No. 61/241,375, filed on Sep. 10, 2009, provisional application No. 61/244,884, filed on Sep. 23, 2009, provisional application No. 61/267,334, filed on Dec. 7, 2009, provisional application No. 61/295,247, filed on Jan. 15, 2010.

(51) Int. Cl.
*A61M 31/00* (2006.01)
*A61M 5/142* (2006.01)
(Continued)

(52) U.S. Cl.
CPC ........... *A61M 5/14244* (2013.01); *A61M 5/148* (2013.01); *A61M 5/1723* (2013.01); *A61M 2205/0272* (2013.01); *A61M 2205/0277* (2013.01)

(58) Field of Classification Search
CPC ................. A61M 2205/0272; A61M 5/14244; A61M 5/148; A61M 5/1723
USPC .................................................... 604/131, 66
See application file for complete search history.

(56) References Cited

U.S. PATENT DOCUMENTS

| 3,922,328 | A | 11/1975 | Johnson | |
| 4,034,380 | A | 7/1977 | Isayama | ........................ 347/19 |

(Continued)

FOREIGN PATENT DOCUMENTS

| CA | 2 477 181 | 4/2004 | |
| CN | 1080829 | 3/2002 | ............. F04B 35/00 |

(Continued)

OTHER PUBLICATIONS

Office Action issued Nov. 23, 2012 in U.S. Appl. No. 12/745,880 (26 pgs.).
(Continued)

*Primary Examiner* — Kevin C Sirmons
*Assistant Examiner* — Deanna K Hall
(74) *Attorney, Agent, or Firm* — Hayes Soloway P.C.

(57) ABSTRACT

A polymer actuator, power supply and method of using the activation are described.

22 Claims, 20 Drawing Sheets

SECTION AA

(51) Int. Cl.
*A61M 5/148* (2006.01)
*A61M 5/172* (2006.01)

(56) References Cited

U.S. PATENT DOCUMENTS

| | | | |
|---|---|---|---|
| 4,111,202 A | 9/1978 | Theeuwes | |
| 4,190,411 A | 2/1980 | Fujimoto | |
| 4,203,440 A | 5/1980 | Theeuwes | |
| 4,299,220 A | 11/1981 | Dorman | 604/118 |
| 4,327,725 A | 5/1982 | Cortese et al. | 424/427 |
| 4,395,719 A | 7/1983 | Majewski et al. | 347/68 |
| 4,423,166 A | 12/1983 | Moriarty et al. | 523/414 |
| 4,432,699 A | 2/1984 | Beckman et al. | 417/63 |
| 4,449,893 A | 5/1984 | Beckman | 417/322 |
| 4,449,983 A | 5/1984 | Cortese et al. | 604/892 |
| 4,507,363 A | 3/1985 | Chow et al. | 428/418 |
| 4,538,607 A | 9/1985 | Saul | 128/207.16 |
| 4,551,139 A | 11/1985 | Plaas et al. | |
| 4,559,038 A | 12/1985 | Berg et al. | |
| 4,595,583 A | 6/1986 | Eckenhoff et al. | |
| 4,624,847 A | 11/1986 | Ayer et al. | |
| 4,624,848 A | 11/1986 | Lee | |
| 4,650,469 A | 3/1987 | Berg et al. | |
| 4,655,767 A | 4/1987 | Woodward et al. | |
| 4,663,149 A | 5/1987 | Eckenhoff et al. | |
| 4,675,174 A | 6/1987 | Eckenhoff | |
| 4,723,958 A | 2/1988 | Pope et al. | |
| 4,772,474 A | 9/1988 | Eckenhoff et al. | |
| 4,781,714 A | 11/1988 | Eckenhoff et al. | |
| 4,808,084 A | 2/1989 | Tsubouchi et al. | 417/322 |
| 4,810,535 A | 3/1989 | McCollum et al. | 427/410 |
| 4,842,493 A | 6/1989 | Nilsson | 417/322 |
| 4,863,456 A | 9/1989 | Stephens et al. | |
| 4,948,592 A | 8/1990 | Ayer et al. | |
| 4,963,141 A | 10/1990 | Eckenhoff | |
| 5,000,957 A | 3/1991 | Eckenhoff et al. | |
| 5,034,229 A | 7/1991 | Magruder et al. | |
| 5,037,420 A | 8/1991 | Magruder et al. | |
| 5,059,423 A | 10/1991 | Magruder et al. | |
| 5,061,242 A | 10/1991 | Sampson | |
| 5,070,560 A | 12/1991 | Wilkinson | 5/455 |
| 5,100,933 A | 3/1992 | Tanaka et al. | 523/300 |
| 5,105,983 A | 4/1992 | Sancoff | 222/103 |
| 5,110,596 A | 5/1992 | Magruder et al. | |
| 3,029,743 A | 3/1993 | Johns | 103/150 |
| 5,192,197 A | 3/1993 | Culp | 417/322 |
| 5,192,298 A | 3/1993 | Culp | F04B 35/04 |
| 5,232,702 A | 8/1993 | Pfister et al. | |
| 5,246,705 A | 9/1993 | Venkatraman et al. | |
| 5,279,544 A | 1/1994 | Gross et al. | |
| 5,279,565 A | 1/1994 | Klein et al. | |
| 5,284,133 A | 2/1994 | Burns et al. | |
| 5,300,299 A | 4/1994 | Sweet et al. | |
| 5,304,121 A | 4/1994 | Sahatjian | |
| 5,327,041 A | 7/1994 | Culp | 310/328 |
| 5,328,696 A | 7/1994 | Noel | |
| 5,336,057 A | 8/1994 | Fukuda et al. | 417/395 |
| 5,348,746 A | 9/1994 | Dong et al. | |
| 5,354,264 A | 10/1994 | Bae et al. | |
| 5,376,378 A | 12/1994 | Li et al. | |
| 5,380,760 A | 1/1995 | Wendel et al. | |
| 5,412,821 A | 5/1995 | Wilkinson | 5/455 |
| 5,429,585 A | 7/1995 | Liang | 601/15 |
| 5,431,921 A | 7/1995 | Thombre | |
| 5,474,783 A | 12/1995 | Miranda et al. | |
| 5,498,255 A | 3/1996 | Wong | |
| 5,546,932 A | 8/1996 | Galli | |
| 5,573,668 A | 11/1996 | Grosh et al. | |
| 5,587,237 A | 12/1996 | Korpman et al. | |
| RE35,474 E | 3/1997 | Woodard et al. | |
| 5,618,899 A | 4/1997 | Appelt et al. | |
| 5,622,482 A | 4/1997 | Lee | 417/321 |
| 5,630,709 A | 5/1997 | Bar-Cohen | 417/322 |
| 5,633,009 A | 5/1997 | Kenealy et al. | |
| 5,645,855 A | 7/1997 | Lorenz | |
| 5,656,286 A | 8/1997 | Miranda et al. | |
| 5,674,192 A | 10/1997 | Sahatjian et al. | |
| 5,687,748 A | 11/1997 | Conrad et al. | |
| 5,692,256 A | 12/1997 | Kramer et al. | 5/624 |
| 5,714,160 A | 2/1998 | Magruder et al. | |
| 5,718,700 A | 2/1998 | Edgren et al. | |
| 5,779,668 A | 7/1998 | Grabenkort | |
| 5,798,600 A | 8/1998 | Sager et al. | 310/330 |
| 5,810,001 A | 9/1998 | Genga et al. | 128/202.27 |
| 5,823,178 A | 10/1998 | Lloyd et al. | |
| 5,891,463 A | 4/1999 | Bello et al. | |
| 5,916,968 A | 6/1999 | Hariharan et al. | |
| 5,939,477 A | 8/1999 | Pretzer et al. | |
| 5,951,999 A | 9/1999 | Therriault et al. | |
| 5,954,706 A | 9/1999 | Sahatjian | |
| 5,961,298 A | 10/1999 | Bar-Cohen | 417/322 |
| 5,979,892 A | 11/1999 | Smith | 271/267 |
| 5,997,501 A | 12/1999 | Gross et al. | |
| 6,004,115 A | 12/1999 | Da Costa | F04B 17/00 |
| 6,010,485 A | 1/2000 | Buch-Rasmussen et al. | |
| 6,024,976 A | 2/2000 | Miranda et al. | |
| 6,066,325 A | 5/2000 | Wallace et al. | |
| RE36,754 E | 6/2000 | Noel | |
| 6,074,178 A | 6/2000 | Bishop et al. | 417/322 |
| 6,074,179 A | 6/2000 | Jokela | 417/322 |
| 6,106,245 A | 8/2000 | Cabuz | 417/322 |
| 6,109,852 A | 8/2000 | Shahinpoor et al. | 414/1 |
| 6,143,138 A | 11/2000 | Becker | 204/157.15 |
| 6,152,898 A | 11/2000 | Olsen | |
| 6,157,113 A | 12/2000 | Hunter et al. | 310/300 |
| 6,165,155 A | 12/2000 | Jacobsen et al. | |
| 6,174,546 B1 | 1/2001 | Therriault et al. | |
| 6,180,133 B1 | 1/2001 | Quan et al. | |
| 6,183,434 B1 | 2/2001 | Eppstein | |
| 6,184,608 B1 | 2/2001 | Cabuz | 310/309 |
| 6,193,996 B1 | 2/2001 | Effing et al. | |
| 6,206,850 B1 | 3/2001 | O'Neil | |
| 6,210,712 B1 | 4/2001 | Edgren et al. | |
| 6,213,739 B1 | 4/2001 | Phallen et al. | 417/478 |
| 6,221,383 B1 | 4/2001 | Miranda et al. | |
| 6,223,369 B1 | 5/2001 | Maier et al. | 5/713 |
| 6,249,076 B1 | 6/2001 | Madden et al. | 310/363 |
| 6,277,401 B1 | 8/2001 | Bello et al. | |
| 6,312,715 B1 | 11/2001 | Cantor et al. | |
| 6,316,022 B1 | 11/2001 | Mantelle et al. | |
| 6,319,245 B1 | 11/2001 | Berrigan | |
| 6,336,907 B1 | 1/2002 | Dono et al. | 601/150 |
| 6,337,086 B1 | 1/2002 | Kanios et al. | |
| 6,352,715 B1 | 3/2002 | Hwang et al. | |
| 6,365,178 B1 | 4/2002 | Venkateshwaran et al. | |
| 6,365,185 B1 | 4/2002 | Ritschel et al. | |
| 6,368,318 B1 | 4/2002 | Visuri et al. | |
| 6,378,292 B1 | 4/2002 | Youngner | 60/224 |
| 6,387,077 B1 | 5/2002 | Klibanov et al. | |
| 6,392,777 B1 | 5/2002 | Elliott et al. | 359/244 |
| 6,409,716 B1 | 6/2002 | Sahatjian et al. | |
| 6,450,773 B1 | 9/2002 | Upton | 417/53 |
| 6,461,644 B1 | 10/2002 | Jackson et al. | |
| 6,464,476 B2 | 10/2002 | Ross et al. | 417/478 |
| 6,471,686 B1 | 10/2002 | Berrigan | |
| 6,475,639 B2 | 11/2002 | Shahinpoor et al. | 428/614 |
| 6,490,483 B2 | 12/2002 | Wallis | 604/20 |
| 6,531,152 B1 | 3/2003 | Lerner et al. | |
| 6,537,194 B1 | 3/2003 | Winkler | |
| 6,578,245 B1 | 6/2003 | Chatterjee et al. | 29/25.35 |
| 6,632,522 B1 | 10/2003 | Hyde et al. | |
| 6,664,718 B2 | 12/2003 | Pelrine et al. | 310/800 |
| 6,682,318 B2 | 1/2004 | Takeuchi | 417/322 |
| 6,682,500 B2 | 1/2004 | Soltanpour et al. | 604/9 |
| 6,685,442 B2 | 2/2004 | Chinn et al. | 417/321 |
| 6,726,678 B1 | 4/2004 | Nelson | 604/891.1 |
| 6,766,817 B2 | 7/2004 | Da Silva | F04F 10/00 |
| 6,791,003 B1 | 9/2004 | Choi et al. | |
| 6,796,970 B1 | 9/2004 | Klitmose et al. | |
| 6,809,462 B2 | 10/2004 | Pelrine et al. | 310/319 |
| 6,864,295 B2 | 3/2005 | Mitarai | 521/50.5 |
| 6,869,275 B2 | 3/2005 | Dante et al. | 417/413.2 |
| 6,876,135 B2 | 4/2005 | Pelrine et al. | 310/339 |
| 6,902,704 B2 | 6/2005 | Wilson | 422/100 |

(56) References Cited

U.S. PATENT DOCUMENTS

| | | | |
|---|---|---|---|
| 6,940,211 B2 | 9/2005 | Pelrine et al. ............... 310/330 |
| 6,948,636 B1 | 9/2005 | Fischer et al. ............... 222/103 |
| 6,949,079 B1 | 9/2005 | Westberg et al. ........... 604/6.11 |
| 6,955,923 B2 | 10/2005 | Hartting ...................... 436/180 |
| 6,960,864 B2 | 11/2005 | Urano et al. .................. 310/307 |
| 7,285,255 B2 | 10/2007 | Kadlec et al. ............... A61L 2/16 |
| 7,411,792 B2 | 8/2008 | Richards et al. ............. 361/704 |
| 7,453,187 B2 | 11/2008 | Richards et al. ............. 310/339 |
| 7,544,260 B2 | 6/2009 | Banister et al. .................. 149/2 |
| 7,553,903 B2 | 6/2009 | Riegel et al. .................. 524/599 |
| 7,700,129 B2 | 4/2010 | Ito et al. ........................ 424/486 |
| 7,820,427 B2 | 10/2010 | Unger et al. ............... 435/286.5 |
| 8,190,270 B2 | 5/2012 | Wingeier et al. ............. 607/116 |
| 2001/0053383 A1 | 12/2001 | Miranda et al. |
| 2002/0004064 A1 | 1/2002 | Quan et al. |
| 2002/0007014 A1 | 1/2002 | Hyde et al. |
| 2002/0010412 A1 | 1/2002 | Eppstein |
| 2002/0015733 A1 | 2/2002 | Flashner-Barak et al. |
| 2002/0043895 A1 | 4/2002 | Richards et al. ............. 310/328 |
| 2002/0106402 A1 | 8/2002 | Hartwig |
| 2002/0115740 A1 | 8/2002 | Beuhler et al. ............... 522/152 |
| 2002/0128572 A1 | 9/2002 | Chang ......................... 601/148 |
| 2002/0128618 A1 | 9/2002 | Frenz et al. .................. 604/368 |
| 2002/0147208 A1 | 10/2002 | Fleshner-Barak et al. |
| 2002/0156463 A1 | 10/2002 | Berrigan |
| 2002/0173745 A1 | 11/2002 | Santini et al. .................... 604/67 |
| 2002/0183738 A1 | 12/2002 | Chee et al. |
| 2002/0193754 A1 | 12/2002 | Cho |
| 2003/0014036 A1 | 1/2003 | Varner et al. |
| 2003/0051292 A1 | 3/2003 | Ferrand et al. ................... 5/600 |
| 2003/0054025 A1 | 3/2003 | Cantor et al. |
| 2003/0065303 A1 | 4/2003 | Wellman et al. |
| 2003/0069359 A1 | 4/2003 | Torii et al. ..................... 525/178 |
| 2003/0072792 A1 | 4/2003 | Flanigan et al. |
| 2003/0108590 A1 | 6/2003 | Peery et al. |
| 2003/0124189 A1 | 7/2003 | Zentner et al. |
| 2003/0135158 A1 | 7/2003 | Gonnelli |
| 2003/0139495 A1 | 7/2003 | Zentner et al. |
| 2003/0143257 A1 | 7/2003 | Fleshner-Barak et al. |
| 2003/0152616 A1 | 8/2003 | Hartwig |
| 2003/0153900 A1 | 8/2003 | Aceti et al. |
| 2003/0156953 A1 | 8/2003 | Chinn et al. .................. 417/332 |
| 2003/0163099 A1 | 8/2003 | Wermeling et al. |
| 2003/0216683 A1 | 11/2003 | Shekalim |
| 2003/0232198 A1 | 12/2003 | Lamberti et al. |
| 2004/0030262 A1 | 2/2004 | Fisher et al. |
| 2004/0068224 A1* | 4/2004 | Couvillon et al. ............... 604/67 |
| 2004/0092865 A1 | 5/2004 | Flaherty et al. |
| 2004/0102762 A1 | 5/2004 | Gilbert |
| 2004/0106893 A1 | 6/2004 | Hunter |
| 2004/0106894 A1 | 6/2004 | Hunter |
| 2004/0112442 A1 | 6/2004 | Maerkl et al. ................. 137/597 |
| 2004/0133159 A1 | 7/2004 | Haider et al. |
| 2004/0138603 A1 | 7/2004 | Cleary et al. |
| 2004/0142023 A1 | 7/2004 | Hartwig |
| 2004/0149288 A1 | 8/2004 | Koch |
| 2004/0176502 A1 | 9/2004 | Raymond et al. ............. 523/416 |
| 2004/0176748 A1 | 9/2004 | Abramson et al. |
| 2004/0186419 A1 | 9/2004 | Cho |
| 2004/0202708 A1 | 10/2004 | Roehrig et al. |
| 2004/0204677 A1 | 10/2004 | Wellman et al. |
| 2004/0219194 A1 | 11/2004 | Finckh et al. |
| 2004/0220548 A1 | 11/2004 | Heruth et al. |
| 2004/0234401 A1 | 11/2004 | Banister ........................ 417/474 |
| 2004/0242709 A1 | 12/2004 | Oguro et al. ..................... 521/27 |
| 2004/0265545 A1 | 12/2004 | McKean et al. ............... 428/189 |
| 2005/0033230 A1 | 2/2005 | Alchas et al. |
| 2005/0043657 A1 | 2/2005 | Couvillon ..................... 601/134 |
| 2005/0058695 A1 | 3/2005 | Anigbogu et al. |
| 2005/0137577 A1 | 6/2005 | Heruth et al. |
| 2005/0137578 A1 | 6/2005 | Heruth et al. |
| 2005/0137579 A1 | 6/2005 | Heruth et al. |
| 2005/0261631 A1 | 11/2005 | Clarke et al. |
| 2005/0273081 A1 | 12/2005 | Olsen |
| 2005/0273082 A1 | 12/2005 | Olsen |
| 2005/0287214 A1 | 12/2005 | Ayer et al. |
| 2006/0021614 A1 | 2/2006 | Wermeling et al. |
| 2006/0076540 A1 | 4/2006 | Zama et al. .................... 252/500 |
| 2006/0078603 A1 | 4/2006 | Nguyen |
| 2006/0078604 A1 | 4/2006 | Kanios et al. |
| 2006/0084942 A1 | 4/2006 | Kim et al. |
| 2006/0089619 A1 | 4/2006 | Ginggen ..................... 604/891.1 |
| 2006/0094985 A1 | 5/2006 | Aceti et al. |
| 2006/0094989 A1 | 5/2006 | Scott et al. ........................ 601/5 |
| 2006/0110596 A1 | 5/2006 | Palasz et al. |
| 2006/0135911 A1 | 6/2006 | Mittur |
| 2006/0142875 A1 | 6/2006 | Keyes et al. ....................... 700/1 |
| 2006/0183216 A1 | 8/2006 | Handique et al. .......... 435/287.1 |
| 2006/0188558 A1 | 8/2006 | Jackson et al. |
| 2006/0200083 A1 | 9/2006 | Freyman et al. ............... 604/181 |
| 2006/0204532 A1 | 9/2006 | John |
| 2006/0213674 A1 | 9/2006 | Dierker, Jr. et al. |
| 2006/0276744 A1 | 12/2006 | Falk |
| 2007/0021697 A1 | 1/2007 | Ginther et al. |
| 2007/0031495 A1 | 2/2007 | Eppstein et al. |
| 2007/0052139 A1 | 3/2007 | Gilbert |
| 2007/0078376 A1 | 4/2007 | Smith |
| 2007/0082038 A1 | 4/2007 | Gale et al. |
| 2007/0088267 A1 | 4/2007 | Shekalim |
| 2007/0092570 A1 | 4/2007 | Missel et al. |
| 2007/0098771 A1 | 5/2007 | Audett et al. |
| 2007/0098772 A1 | 5/2007 | Westcott et al. |
| 2007/0100355 A1 | 5/2007 | Bonde et al. |
| 2007/0104771 A1 | 5/2007 | Audett et al. |
| 2007/0134310 A1 | 6/2007 | Nedberge et al. |
| 2007/0148218 A1 | 6/2007 | Gordon |
| 2007/0190150 A1 | 8/2007 | Ito et al. ........................ 424/486 |
| 2007/0224253 A1 | 9/2007 | Franklin |
| 2007/0260201 A1 | 11/2007 | Prausnitz et al. |
| 2007/0269522 A1 | 11/2007 | Wold |
| 2007/0293826 A1 | 12/2007 | Wall et al. |
| 2008/0009800 A1 | 1/2008 | Nickel |
| 2008/0015494 A1 | 1/2008 | Santini, Jr. et al. |
| 2008/0033228 A1 | 2/2008 | Rastegar et al. ................. 600/16 |
| 2008/0039791 A1 | 2/2008 | Abboud et al. ............... 604/113 |
| 2008/0058706 A1 | 3/2008 | Zhang et al. |
| 2008/0063698 A1 | 3/2008 | Hartwig |
| 2008/0091139 A1 | 4/2008 | Srinivasan et al. .............. 604/68 |
| 2008/0110463 A1 | 5/2008 | Hajgato et al. |
| 2008/0125744 A1 | 5/2008 | Treacy |
| 2008/0152592 A1 | 6/2008 | Rebec |
| 2008/0167641 A1 | 7/2008 | Hansen et al. |
| 2008/0183144 A1 | 7/2008 | Trautman et al. |
| 2008/0195018 A1 | 8/2008 | Larson et al. .................... 602/53 |
| 2008/0208107 A1 | 8/2008 | McRae et al. |
| 2008/0214987 A1 | 9/2008 | Xu |
| 2008/0221552 A1 | 9/2008 | Leonard |
| 2008/0234656 A1 | 9/2008 | Pettis et al. |
| 2008/0312610 A1 | 12/2008 | Binks et al. |
| 2008/0317615 A1 | 12/2008 | Banister ..................... 417/413.1 |
| 2009/0007904 A1 | 1/2009 | Schuster et al. |
| 2009/0020521 A1 | 1/2009 | Blaszczykiewicz et al. . 219/529 |
| 2009/0026069 A1 | 1/2009 | Liao et al. ..................... 204/274 |
| 2009/0041833 A1 | 2/2009 | Bettinger et al. |
| 2009/0042970 A1 | 2/2009 | Herschkowitz et al. |
| 2009/0048555 A1 | 2/2009 | Stryker et al. |
| 2009/0060986 A1 | 3/2009 | Yum et al. |
| 2009/0085444 A1 | 4/2009 | Alvarez Icaza Rivera et al. ............................ 310/365 |
| 2009/0099545 A1 | 4/2009 | Nilsson et al. |
| 2009/0118662 A1 | 5/2009 | Schnall |
| 2009/0221971 A1 | 9/2009 | Mejlhede et al. |
| 2009/0227988 A1 | 9/2009 | Wood, Jr. et al. ........... 604/891.1 |
| 2009/0232685 A1 | 9/2009 | Kamitani et al. .......... 417/413.2 |
| 2009/0317442 A1 | 12/2009 | Banister et al. ............... 424/423 |
| 2010/0004638 A1 | 1/2010 | Gibson ....................... 604/891.1 |
| 2010/0074953 A1 | 3/2010 | Chaouk et al. ................ 424/484 |
| 2011/0172645 A1 | 7/2011 | Moga et al. |

FOREIGN PATENT DOCUMENTS

| | | | |
|---|---|---|---|
| CN | 1934776 A | 3/2007 | ............ H02N 11/00 |
| DE | 199 12 606 | 12/2000 | ............ F04B 43/04 |
| EP | 0 723 982 | 7/1996 | ............ C08G 59/56 |

(56) References Cited

FOREIGN PATENT DOCUMENTS

| | | | |
|---|---|---|---|
| EP | 0 736 556 | 9/1996 | ............ C08G 59/00 |
| EP | 0882890 | 12/1998 | ............ F04B 45/053 |
| EP | 1 454 935 | 8/2004 | ............ C08G 59/00 |
| JP | 58-25326 | 2/1983 | |
| JP | 60-235847 | 11/1985 | |
| JP | 02-004826 | 1/1990 | |
| JP | 02 137 930 | 5/1990 | ................ B41J 2/05 |
| JP | 08-283540 | 10/1996 | |
| JP | 09 287 571 | 11/1997 | ............ F04B 43/04 |
| JP | 2004-514770 | 5/2004 | |
| JP | 2004-261045 | 9/2004 | |
| JP | 2004-269882 | 9/2004 | |
| JP | 2005269773 | 9/2005 | ................ F03G 7/00 |
| JP | 2006353034 | 12/2006 | ................ H02N 2/00 |
| JP | 2008211915 | 9/2008 | ................ F03G 7/00 |
| JP | 2009046649 | 3/2009 | ............ C08F 12/34 |
| WO | WO 96/17170 | 6/1996 | ............ F04B 35/00 |
| WO | WO 96/20971 | 11/1996 | ............ C08G 63/00 |
| WO | WO 97/42412 | 11/1997 | ............ F04B 43/12 |
| WO | WO 00/28215 | 5/2000 | ............ F04B 45/047 |
| WO | WO 02/44240 | 6/2002 | ............ C08G 59/40 |
| WO | WO 2004/031581 | 4/2004 | |
| WO | WO 2004/076859 | 9/2004 | ............ F04B 43/04 |
| WO | WO 2005/061014 | 7/2005 | |
| WO | WO 2005/118008 | 12/2005 | |
| WO | WO 2006/065884 | 6/2006 | |
| WO | WO 2008/079440 | 7/2008 | ............ C08L 63/10 |
| WO | WO 2009/069086 | 4/2009 | |

OTHER PUBLICATIONS

"An Electrochemical Microactuator: Principle and First Results", Neagu et al. Journal of Microelectromechanical Systems, vol. 5, No. 1. Mar. 1996 (7 pgs).
"ElectroActive Polymers—EAPs," downloaded from http://www.azom.com on Dec. 16, 2013 (5 pgs).
"Epoxy-Based Electroactive Polymer Gels", Yoshioka Y and Calvert P, Experimental Mechanics, vol. 42, No. 4, Dec. 2002, pp. 404-408 (5 pgs).
"Magnetic Driven Compression Cascade and Packaging", IBM Technical Disclosure Bulletin, IBM Corp., col. 38, co. 1, Jan. 1995 (3 pgs).
"Micro-Dispensing Positive Displacement Pump", Anonymous, Research Disclosure, Mason Publications, Hampshire GB, vol. 374, No. 4, Jun. 1995 (9 pgs).
"Structure and Mechanism of Two Types of Micro-Pump Using Polymer Gel", Hattori et al., Micro Electro Mechanical Systems, 1992, MEMS 92, Proceedings. An Investigation of Micro Structures, Sensors, Actuators, Machines and Robot, IEEE Travemunde, Germany, Feb. 1992 (6 pgs).
Bar-Cohen, Y., "Electroactive polymers (EAP) actuators as artificial muscles: reality, potential and challenges," SPIE Press, 2001, 671 pgs, (book description only, 4 pgs).
Canadian Official Action issued in Appln. No. 2,557,325, dated Feb. 8, 2011 (5 pgs).
Chinese Notification of ReExamination and English translation, Appln. or Pat. No. 200580048306.3; dated Aug. 22, 2014 (11 pgs).
Chinese Office Action (w/English translation) issued in corresponding application No. 200780032137.3, dated Mar. 12, 2013 (14 pgs).
Chinese Office Action and Translation dated Jul. 6, 2011 issued in Chinese Patent Appln. No. 200780032137.3 (7 pgs).
Chinese Office Action issued Jul. 1, 2014 with English translation, Appln. No. or Patent No. 201180007957.3 (17 pgs).
Chinese Office Action, Application/Patent No. 200780032137.3, dated Dec. 23, 2011 (6 pgs).
Chinese Official Action + translation dated Feb. 1, 2011 issued in Appln. No. 200780032137.3, (8 pgs).
Chinese Official Action dated Mar. 17, 2011, Appln. No. 200580048306.3 (5 pgs).
Chinese Official Action issued in corresponding Chinese Patent Appln. Serial No. 200580048306.3 dated Nov. 4, 2011 (5 pgs).

European Office Action dated Sep. 14, 2010, Appln. No. 07 872 242.8-2102, (6 pgs).
European Official Action issued in Appln. No. 04714231.0, dated May 11, 2011 (2 pgs).
European Official Action issued in Appln. No. 04714231.0-2315/1611353, dated Oct. 4, 2010 (4 pgs).
European Official Action, Apr. 6, 2011 issued in Appln. No. 07 872 242.8-2102 (4 pages).
European Official Action, Aug. 29, 2011 issued in Appln. No. 07 872 242.8-2102 (6 pages).
European Search Report dated Feb. 18, 2011 issued in corresponding Appln. No. 10014840.2-2315 (7 pgs).
European Search Report dated Jun. 8, 2009, Serial No. 07872242.8-2102 (7 pgs).
First Examination Report dated Dec. 31, 2013, Indian Patent Application No. 3011/CHENP/2007 (2 pgs).
Indian Examination Report; Indian Patent Application Serial No. 2371/CHENP/2005, dated Sep. 7, 2006 (2 pgs).
International Preliminary Report on Patentability issued in PCT/US10/48489 dated Mar. 13, 2012 (12 pgs).
International Search Report and Written Opinion issued in corresponding PCT Patent Appln. Serial No. PCT/US2012/057129 dated Apr. 1, 2014 (7 pgs).
International Search Report and Written Opinion of the International Search Authority issued in PCT/US09/34557, dated Apr. 13, 2009 (6 pgs).
Japanese Office Action with translation, Patent Appln. 2009-519642, dated Jul. 9, 2012 (9 pgs).
Office Action issued in related U.S. Appl. No. 10/786,718, dated Mar. 5, 2008 (41 pgs).
Office Action issued in related U.S. Appl. No. 10/786,718, dated Sep. 16, 2008 (8 pgs).
Office Action issued in related U.S. Appl. No. 10/786,718, dated Jan. 2, 2009 (9 pgs).
Office Action issued in related U.S. Appl. No. 10/786,718, dated Jul. 1, 2009 (7 pgs).
Office Action issued in related U.S. Appl. No. 10/786,718, dated Dec. 28, 2009 (6 pgs).
Office Action issued in related U.S. Appl. No. 10/786,718, dated May 5, 2010 (7 pgs).
Office Action issued in related U.S. Appl. No. 10/786,718, dated Sep. 15, 2010 (8 pgs).
Office Action issued in related U.S. Appl. No. 10/786,718, dated Nov. 23, 2010 (10 pgs).
Office Action issued in related U.S. Appl. No. 11/254,537, dated Sep. 17, 2007 (8 pgs).
Office Action issued in related U.S. Appl. No. 11/254,537, dated Mar. 4, 2008 (8 pgs).
Office Action issued in related U.S. Appl. No. 11/254,537, dated Jul. 21, 2008 (10 pgs).
Office Action issued in related U.S. Appl. No. 11/254,537, dated Dec. 15, 2008 (8 pgs).
Office Action issued in related U.S. Appl. No. 12/373,245, dated Feb. 2, 2011 (13 pgs).
Office Action issued in related U.S. Appl. No. 12/373,245, dated Jul. 22, 2011 (11 pgs).
Office Action issued in related U.S. Appl. No. 12/373,245, dated Jun. 30, 2014 (18 pgs).
Office Action issued in related U.S. Appl. No. 12/414,536, dated Nov. 29, 2010 (8 pgs).
Office Action issued in related U.S. Appl. No. 12/978,152, dated May 23, 2011 (9 pgs).
Office Action issued in related U.S. Appl. No. 13/018,024, dated Aug. 7, 2014 (17 pgs).
Office Action issued in related U.S. Appl. No. 13/093,648, dated Aug. 29, 2013 (5 pgs).
Office Action issued in related U.S. Appl. No. 13/424,172, dated Jun. 27, 2012 (14 pgs).
Office Action issued in related U.S. Appl. No. 13/424,172, dated Nov. 9, 2012 (6 pgs).
Office Action issued in related U.S. Appl. No. 14/071,371, dated Aug. 21, 2014 (16 pgs).

(56) References Cited

OTHER PUBLICATIONS

Office Action issued in related U.S. Appl. No. 12/745,880, dated Jun. 3, 2013 (8 pgs).
Official Action received in corresponding Chinese Application No. 200480010203.3, Sep. 14, 2007 (19 pgs).
Official Action received in corresponding Chinese Application No. 200480010203.3, Nov. 14, 2008 (5 pgs).
Official Action received in corresponding EPO Application. No. 04 714 231.0-2315, Nov. 13, 2008 (5 pgs).
Official Action, U.S. Appl. No. 11/721,800, dated Aug. 27, 2010 (13 pgs).
PCT International Preliminary Report on Patentability, dated Aug. 26, 2005, PCT/US04/005922 (11 pgs).
PCT International Search Report and Written Opinion, dated Oct. 22, 2004, PCT/US04/005922 (17 pgs).
PCT International Search Report and International Preliminary Report on Patentability, dated Oct. 25, 2006, PCT/US05/45210 (10 pgs).
PCT International Search Report and International Preliminary Report on Patentability, dated Jul. 7, 2008, PCT/US07/73188 (8 pgs).
PCT International Search Report and International Preliminary Report on Patentability, dated Feb. 19, 2009, PCT/US08/85421 (7 pgs).
PCT International Search Report and Written Opinion dated Mar. 28, 2011 PCT/US11/23375 (10 pgs).
PCT International Preliminary Report on Patentability issued in PCT/US2013/031062, dated Sep. 16, 2014 (9 pgs).
Search Report and Written Opinion received in Applicant's corresponding European Patent Application Serial No. 05854009.7, Nov. 11, 2009 (8 pgs).
Supplemental European Search Report issued in EP04714231, dated Jan. 25, 2007 (2 pgs).
Unsolicited letter from Dr. Elson Silva, dated Oct. 21, 2010 (5 pgs).
Yoshioka et al., "Electrically Driven Miniature Hydrogels as Muscle-Like Acuators", 2001; Proceedings of SPIE vol. 4329, pp. 216-222 (7 pgs).
Office Action issued in related U.S. Appl. No. 14/071,371, dated Dec. 18, 2014 (11 pgs).
Japanese Office Action (with translation) issued in related application No. 2012-551386, dated Jan. 28, 2015 (9 pgs).
Office Action issued in related U.S. Appl. No. 13/395,627, dated Feb. 5, 2015 (7 pgs).
Chinese Board Decision, Appln. No. 200580048306.3, dated Dec. 26, 2014 (14 pgs).
Office Action issued in related U.S. Appl. No. 12/373,245, dated Feb. 9, 2015 (11 pgs).
Office Action issued in related U.S. Appl. No. 12/918,466, dated Jul. 11, 2013 (36 pgs).
India Hearing Notice in Reference of Application No. 3011/CHENP/2007, dated Feb. 5, 2015 (1 pg).
Office Action issued in U.S. Appl. No. 13/018,024, dated Feb. 24, 2015 (12 pgs).
Office Action issued in U.S. Appl. No. 13/424,172, dated Jun. 10, 2015 (14 pgs).
Office Action issued in U.S. Appl. No. 14/347,597, dated Jun. 3, 2015 (12 pgs).
Indian Office Action issued in application No. 137/CHENP/2009, dated Mar. 17, 2015 (2 pgs).
Office Action issued in U.S. Appl. No. 12/745,880, dated Jul. 22, 2015 (16 pgs).
Chinese Office Action issued in application No. 201180007957.3, dated May 22, 2015, with English translation (15 pgs).
Office Action issued in U.S. Appl. No. 13/018,024, dated Aug. 4, 2015 (10 pgs).

* cited by examiner

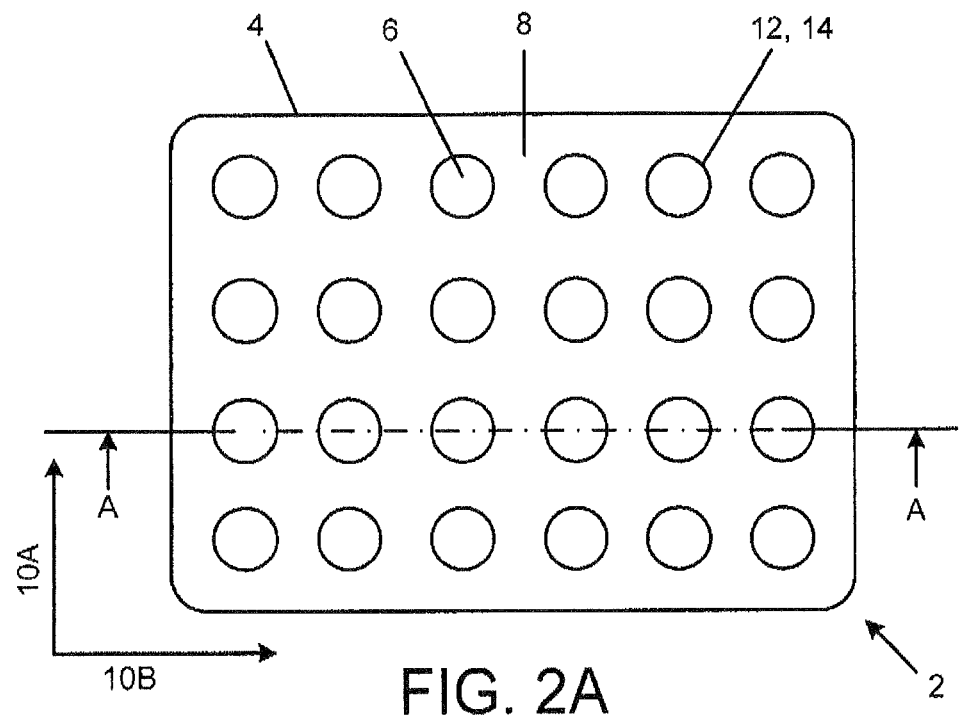
FIG. 2A
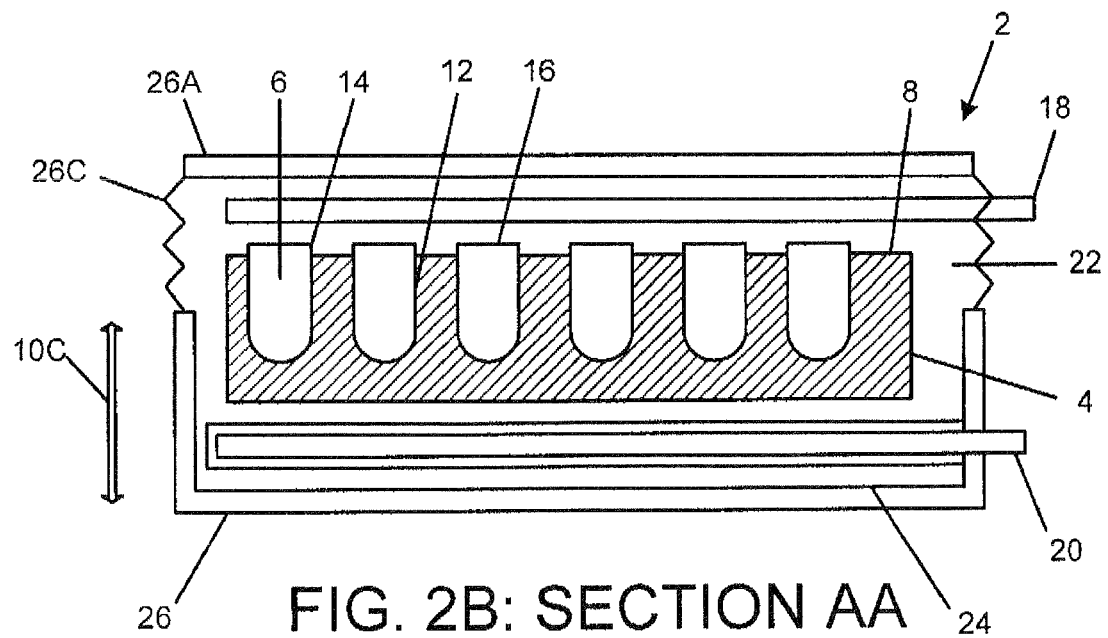
FIG. 2B: SECTION AA

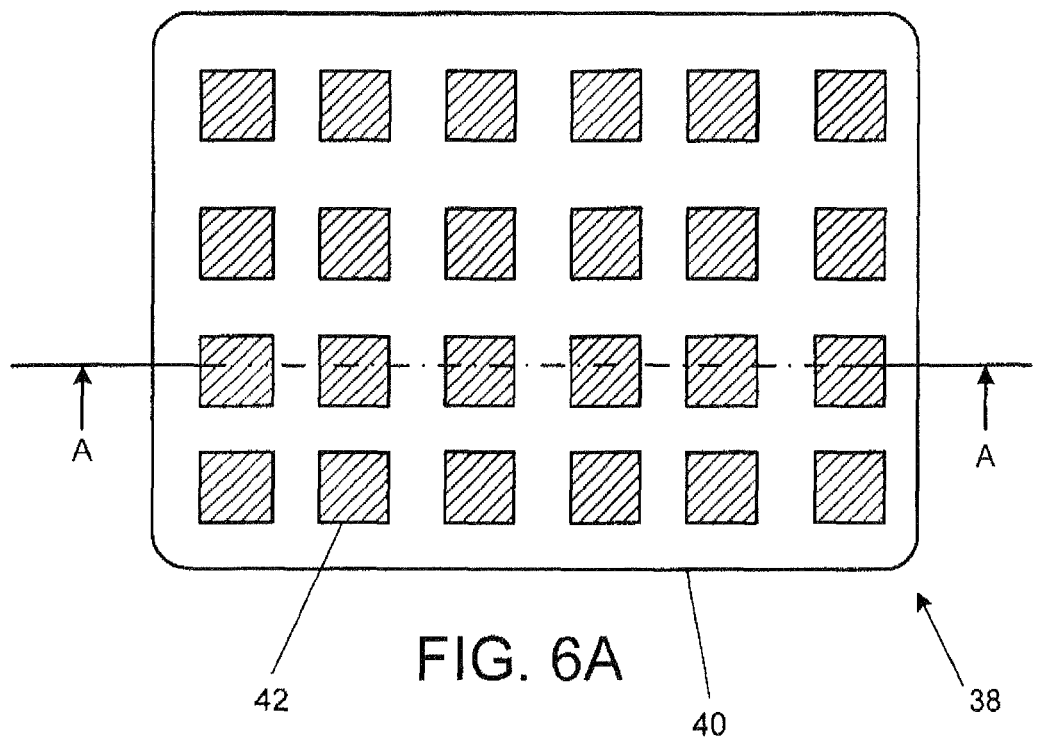
FIG. 6A
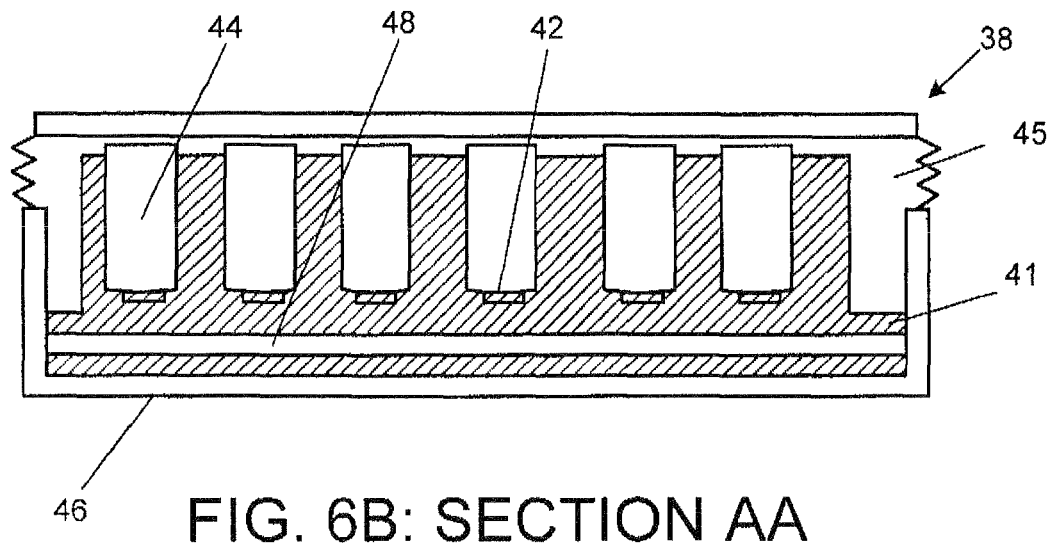
FIG. 6B: SECTION AA

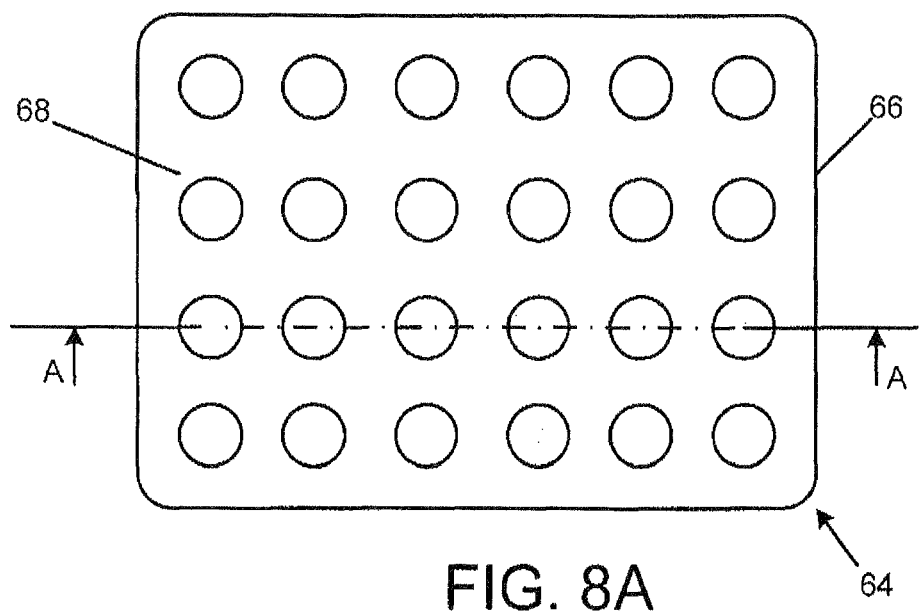
FIG. 8A
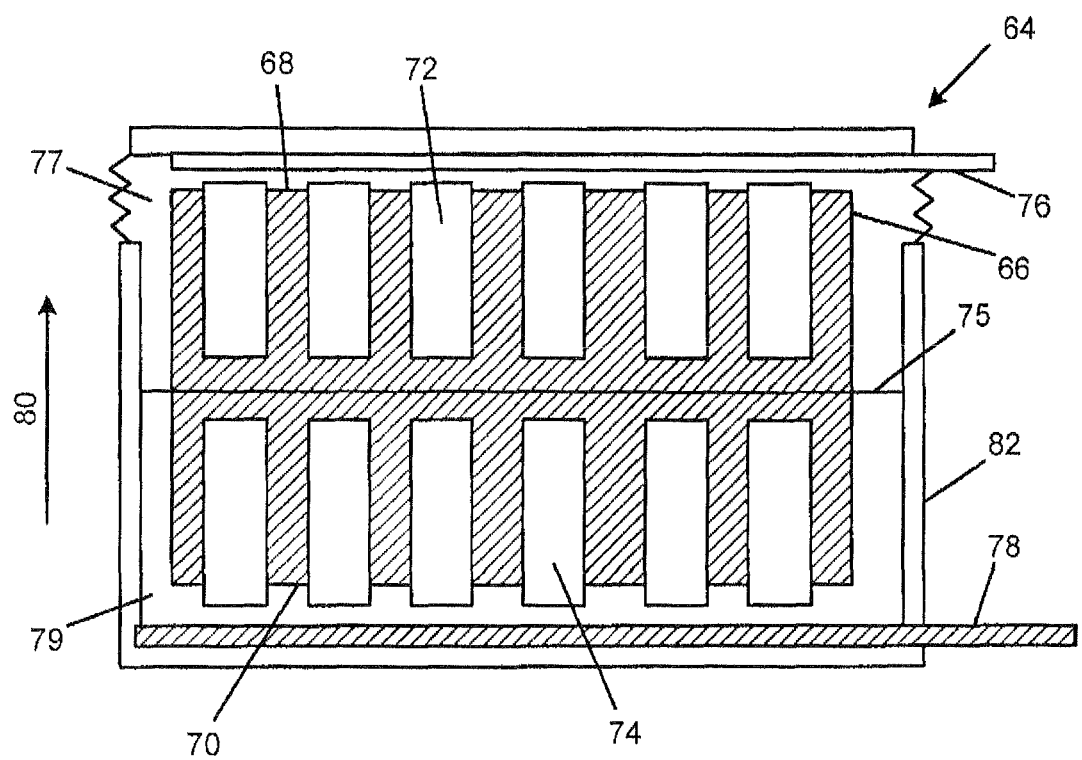
FIG. 8B: SECTION AA

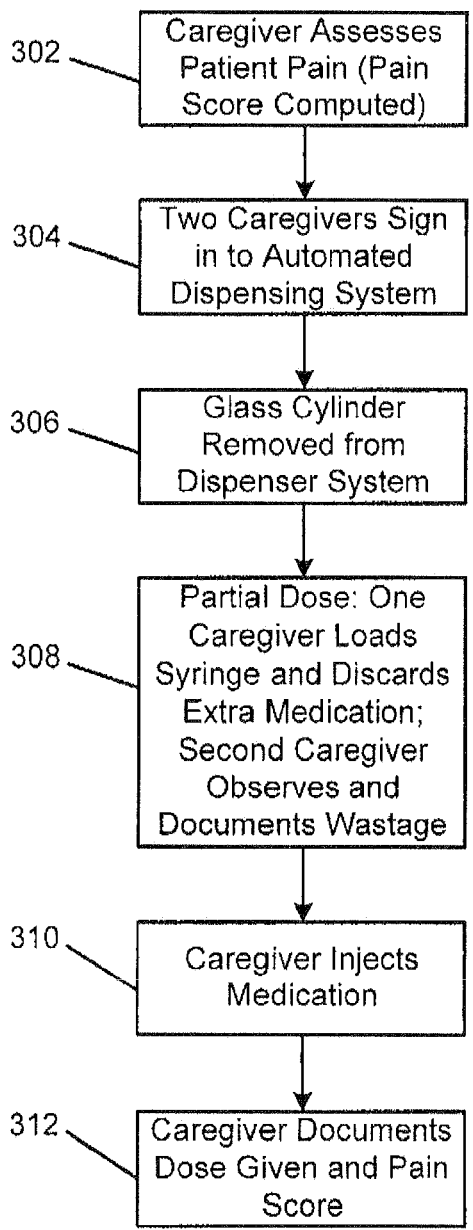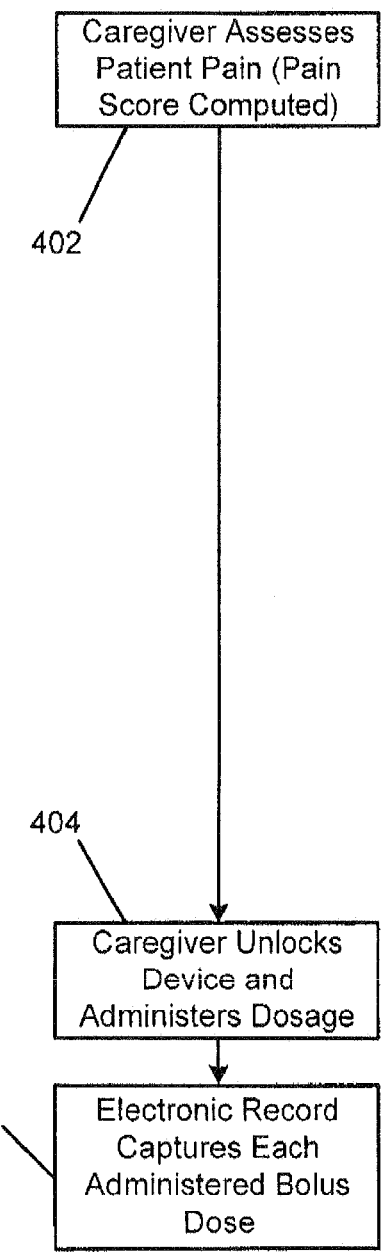
FIG. 19A
PRIOR ART
FIG. 19B

LOW PROFILE ACTUATOR AND IMPROVED METHOD OF CAREGIVER CONTROLLED ADMINISTRATION OF THERAPEUTICS

CROSS REFERENCE TO RELATED APPLICATIONS

This application claims priority from U.S. Provisional Application Ser. Nos. 61/241,375, 61/244,884, 61/267,334 and 61/295,247, filed respectively on Sep. 10, 2009, Sep. 23, 2009, Dec. 7, 2009 and Jan. 15, 2010, the contents of which are incorporated herein in their entireties.

GOVERNMENT SUPPORT

This invention in part was made with U.S. government support under (IIP 0848528) awarded by the National Science Foundation. The U.S. Government may have certain rights in the invention.

FIELD OF THE INVENTION

The present invention in one aspect concerns a low profile actuator assembly. More particularly the actuator of the present invention utilizes a polymeric actuator configured to generate a large linear displacement over an area in response to a change in an ionic concentration of pH of an electrolyte that is in contact with the polymeric actuator, and the use of a porous electrode separator material in such a device. The invention has particular utility in connection with administration of therapeutic liquids and will be described in connection with such utility, although other utilities are contemplated.

In another aspect the invention concerns a low profile actuator assembly of the above type and a power supply that powers the actuator to displace in one or more linear steps over a time period.

In yet another embodiment the present invention concerns a low profile and volumetrically efficient medication delivery device configured to be placed on the body of a patient during fluid delivery to the patient. More particularly the present invention incorporates a low profile area actuator assembly that causes fluid delivery by displacing a collapsible reservoir in response to receiving a current or charge input from a power supply.

In still another aspect, the invention concerns a method for improving the efficiency of caregiver-controlled administration of low or high potency therapeutic liquids and potentially dangerous medications to a patient in a healthcare facility.

BACKGROUND OF THE INVENTION

Actuators are devices that generate displacements or force for various applications. These can take on many forms such as motors, air cylinders, hydraulic cylinders, and electromagnetic solenoids to name a few. These actuators are utilized for many different applications and have been in use for decades.

More recently there have been attempts at developing applications for actuators that require small size and "low profile". By low profile, we mean that the actuator must operate over an area but be spatially constrained in thickness and/or length. This can be quite challenging in the actuator art. An example of such an application is an IV pump that is to be worn by a patient. To avoid discomfort and embarrassment the patient would prefer that such a pump be very thin so as to not be particularly noticeable under clothing or even swim suits.

Conventional actuators do not meet the full need for such an application. There is a need for thinner and lower profile actuators that still meet high performance actuation requirements such as a generation of high forces and displacements. Furthermore the state of the art polymer actuators do not include a separator material to isolate and create distinct ionic or pH boundaries of the electrolyte at the anode or cathode side of the electrodes. This eliminates comingling of the ionic or pH regions, the addition of the separator material substantially increases the response, accuracy, time and volume changes of the actuator material as well as improving the range of electrode materials and configurations of the cathode and anode electrodes within the device.

Patients have need of pumped medication in a variety of settings. Most pumps such as IV pumps are relatively bulky and usually only suitable at a bedside in a managed care environment such as a hospital. More recently medications have been delivered by more portable pumps that may be fastened to the body. Such pumps are more convenient than the larger IV pumps but still suffer from tradeoffs such as limitations on the amount of medication that may be delivered. Moreover, wearing a pump on the body can be quite uncomfortable. There is a need to improve upon these pumps in terms of their comfort and their ability to deliver larger volumes of medication.

Also, critical high potency medications such as Schedule II pain therapeutics are often administered to patients at healthcare facilities. Schedule II pain medications are particularly important for patients having undergone surgeries or having conditions involving acute pain. In such a situation a doctor writes an order or prescription for treatment of the patient. The order is filled or verified by the facility pharmacy and may need to be renewed every 48 to 96 hours. The order can then be dispensed by an automated cabinet system to a caregiver (e.g., a nurse) as required by the patient.

Insufficient or delayed pain therapy may impair a patient's ability to heal and leave the healthcare facility. What is needed is a new process that addresses these issues while simplifying the process of administering the medication.

SUMMARY OF THE INVENTION

The present invention, in one aspect, provides a polymeric actuator assembly comprising: a housing; a carrier having an upper surface within the housing; a plurality of discrete polymeric actuators disposed in an area arrangement across the upper surface; an electrolyte contained in the housing and in contact with the plurality of discrete polymeric actuators; and an apparatus for changing the pH in the electrolyte, wherein each discrete polymeric actuator has a volume that expands in response to the change in pH, and each discrete polymeric actuator is geometrically constrained to cause the expansion to be predominantly in a direction that is directed away from the upper surface.

The present invention also provides, in another aspect, a polymeric actuator assembly comprising: a housing; a carrier having an upper surface and a plurality of wells formed in the carrier, each well opening onto the upper surface; a plurality of polymeric actuators each having a volume that is partially contained in a corresponding one of the wells; an electrolyte solution contained within the housing and in contact with the plurality of polymeric actuators; and an apparatus for modifying the pH within the electrolyte solution.

In yet another aspect, the present invention provides a polymeric actuator assembly comprising: a housing; a polymeric actuator within the housing; a first electrode in contact with the electrolyte; a first electrolyte in contact with the polymeric actuator and the first electrode; a second electrode; a second electrode in contact with the second electrode; and a porous separator configured to separate the first electrolyte from the second electrolyte, wherein the first electrolyte is configured to change in pH in response to current passing between the first electrode to the second electrode, and the polymeric actuator is configured to change volume in response to the change in pH.

The present invention, in another aspect also provides an actuator system comprising: a housing; a polymeric actuator having a volume disposed within the housing; an electrolyte within the housing and in contact with the polymeric actuator; an electrode set within the housing and configured to modulate an ion concentration or pH of the electrolyte in response to charge being passed through the electrode set; and a power supply configured to:

(1) deliver a first positive bias charge through the electrode set during a first time period, the volume is configured to change from a first volume to a second volume in response to the delivery of the first positive bias charge; and (2) deliver a negative bias charge through the electrode set having a magnitude that is less than the first positive bias charge, a rate of change of the volume is configured to be reduced in response to the delivery of the negative bias charge.

Also provided by the present invention is a actuator system comprising: a housing; a polymeric actuator having a volume disposed within the housing; an electrolyte within the housing and in contact with the polymeric actuator; an electrode set within the housing and configured to modulate an ion concentration or pH of the electrolyte in response to charge being passed through the electrode set; and a power supply configured to:

(1) deliver a first positive bias charge through the electrode set during the first time period, the volume is configured to change from a first volume to a second volume in response to the delivery of the first positive bias charge;

(2) pause for a second time period that is longer than the first time period; and (3) deliver a second positive bias charge during a third time period, the second positive bias charge having a greater magnitude than the first positive bias charge.

The present invention further provides an actuator system comprising: a polymeric actuator having a volume; an electrolyte in contact with a polymeric actuator; an electrode set configured to modulate an ion concentration or pH of the electrolyte in response to charge being passed through the electrode set; and a power supply configured to programmably pass charge through the electrode such that the polymeric actuator alternates between relatively short periods of rapid expansion each followed by a relatively longer period with reduced expansion.

Additionally, the present invention provides a method of controlling an expansion of a polymeric actuator comprising: providing a housing containing a polymeric actuator, an electrolyte in contact with polymeric actuator, and an electrode set configured to modulate ion concentration or pH within the electrolyte in response to current being passed through the electrode set, the polymeric actuator having a volume that is responsive to the change in ion concentration or pH; passing a first forward bias charge through the electrode set that is sufficient to change the volume to a second volume; and passing a reverse bias charge through the electrode set that is of smaller magnitude than the forward bias charge and that is sufficient to reduce a rate of change of the volume.

The invention also provides a low profile medication delivery device comprising: a chassis having a first pocket and a second pocket; an actuator assembly overlaying a collapsible reservoir disposed within the first pocket; and electronics disposed within the second pocket and coupled to the actuator assembly, the actuator assembly configured to expand and compress the collapsible reservoir in response to current being passed through the actuator assembly.

In yet another aspect, the present invention provides a method of providing therapeutic liquid device comprising: providing a liquid delivery device comprising: a housing configured to be mounted to a patient body; a reservoir within the housing; a fluid delivery device coupled to the reservoir and configured to deliver fluid to the patient; and a controller having a memory device; selecting a medication type and concentration based upon a particular class of patient conditions; filling the reservoir with the type and concentration of the medication; and storing information on the memory device that defines parameters that govern operation of the fluid delivery device pursuant to safety and efficacy of administration specific to the medication type and concentration.

The invention also provides a therapeutic liquid delivery device comprising: a housing configured to be mounted to a patient body; a reservoir within the housing containing a type of medication having a concentration; a fluid delivery device coupled to the reservoir and configured to delivery fluid to the patient; a controller having a memory device storing information including:

(1) an operating system that is factory loaded that enables all operation of the device; and (2) parameters received from a filling and programming facility that are specific to the medication type and concentration; and a user interface; the controller configured to:

(i) read the information defining the parameters;

(ii) receive inputs from the user interface; and (iii) operate the fluid delivery device to administer the medication to the patient pursuant to the parameters.

The present invention also provides a method of administering a therapeutic fluid comprising: providing a liquid delivery device to a health care facility inventory, the liquid delivery device including:

(1) a housing configured to be mounted to a patient body;

(2) a reservoir within the housing containing a medication having a type and concentration;

(3) a fluid delivery device coupled to the reservoir and configured to deliver fluid to the patient;

(4) a controller having a memory device storing information defining parameters that govern operation of the fluid delivery device according to safety and efficacy of administration of the medication type and concentration; and (5) a user interface;

wherein the controller is configured to:

(i) read the information defining the parameters;

(ii) receive inputs from the user interface; and (iii) operate the fluid delivery device to administer the medication to the patient pursuant to the parameters;

based on a physician order, a caregiver retrieving the liquid delivery device from inventory;

the caregiver placing the housing onto the patient body; the caregiver coupling the fluid delivery device to the patient body; and the caregiver activating the liquid delivery device to deliver the medication to the patient.

The invention also provides an article of manufacture for providing a therapeutic liquid comprising a liquid device comprising: a housing configured to be mounted to a patient body; a reservoir within the housing; a fluid delivery device coupled to the reservoir and configured to delivery fluid to the patient; a user interface; and a controller having a computer readable storage medium having computer readable program code disposed therein for storing information on the memory device that defines parameters that govern operation of the fluid delivery device pursuant to safety and efficacy of administration specific to the medication type and concentration.

In addition, the invention provides an article of manufacture for delivering a therapeutic liquid comprising: a housing configured to be mounted to a patient body; a reservoir within the housing containing a medication; a fluid delivery device coupled to the reservoir and configured to delivery fluid to the patient; a controller having a computer readable storage medium having computer readable program code disposed therein for reading information defining parameters received from a filling and programming facility that are specific to the medication type and concentration; receive inputs from the user interface; and operate the fluid delivery device to administer the medication to the patient pursuant to the parameters.

In yet another embodiment, the invention provides an article of manufacture for administering a therapeutic fluid comprising: a liquid delivery device, the liquid delivery device including: a housing configured to be mounted to a patient body; a reservoir within the housing containing a medication having a type and concentration; a fluid delivery device coupled to the reservoir and configured to deliver fluid to the patient; a user interface; and a controller having computer readable storage medium having computer readable program code for storing information defining parameters that govern operation of the fluid delivery device according to safety and efficacy of administration of the medication type and concentration; the controller configured to: read the information defining the parameters; receive inputs from the user interface; and operate the fluid delivery device to administer the medication to the patient pursuant to the parameters; based on a physician order, a caregiver retrieving the liquid delivery device from inventory.

In still yet another embodiment of the invention, the therapeutic liquid delivery device of the present invention is paired with a patient monitoring device such as, for example, a pulse oximeter, a blood $CO_2$ sensor, a respiration rate sensor; a blood pressure monitor, or a glucose monitor, or the like, with feedback to the liquid delivery device controller to adjust, alarm or stop the pump if the patient is showing signs of overmedication. The feedback also could be used to adjust the pump if the patient is showing signs of undermedication.

BRIEF DESCRIPTION OF THE DRAWINGS

Further features and advantages of the present invention will be seen from the following detailed description, taken into conjunction with the attached drawings, in which like numerals depict like parts, and wherein.

FIG. 2A depicts a plan or area view of an actuator 2 of the present invention with various details missing;

FIG. 2B depicts a cross section taken through actuator 2 along AA depicted in FIG. 2A;

FIG. 6A depicts an alternative actuator assembly 38 including a carrier 40 having a plurality of individually addressable electrodes 42 that each correspond to a polymeric actuator 44;

FIG. 6B depicts a cross section taken through actuator assembly 38 along AA of FIG. 6A;

FIG. 8A depicts an alternative actuator assembly 64 including a "double sided" carrier 66 supporting active reactive discrete polymeric actuators 72 on a first side and base reactive polymeric actuators 74 on a second side;

FIG. 8B depicts a cross section taken through assembly 64 along AA of FIG. 8A;

FIG. 19A depicts a prior art method of delivering medication;

FIG. 19B depicts a new simplified method of delivering medication according to the present invention;

DETAILED DESCRIPTION OF THE PREFERRED EMBODIMENT

Figure 1A:
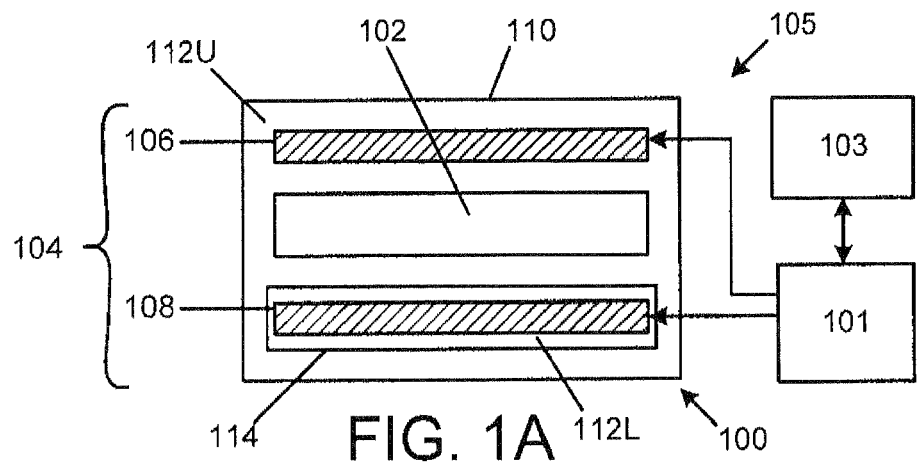
FIG. 1A depicts an exemplary system 100 according to the one aspect of the present invention.

In the following description directional or geometric terms such as "upper", "lower", and "side" are used solely with reference to the orientation of the Figures depicted in the drawings. These are not to imply or be limited to a direction with respect to a gravitational reference frame but are utilized to distinguish directions relative to each other. Because components of the present invention can be positioned in a number of different orientations, the directional terminology is used for purposes of illustration and is in no way limiting. It is to be understood that other embodiments may be utilized and structural or logical changes may be made without departing from the scope of the present invention.

Details in the various embodiments such as how current or wiring is routed to electrodes from power supplies are left out for illustrative simplicity since various methods of such routing is known in the art. The term "electrolyte" refers to and includes all aqueous, non-aqueous, polymer and solid electrolytes, including those that are generally well known in the art. The term "electrodes" refer to anodes and cathodes commonly used in electrochemical systems that are made of materials well known in the art such as metals, carbons, graphenes, oxides or conducting polymers or combinations of these. The term "separator" refers to any nano, micro or macro porous material that allows targeted ions to move through or across it faster than surrounding ion containing media. The term "ion" refers to ions and ion species as well as anion, cation, electrons and protons, and concentration values of these. The term "housing" refers to the exterior portion of the device which may be fabricated from flexible material, rigid material, elastic materials, non elastic materials or a combination of these such as rubbers, silicone, polyurethane, metalized polymer films and other plastics or polymers known in the art. The housing is configured to allow movement and expansion of the internal parts as well as allowing for filling device with electrolyte, acting as a container and barrier to stop any electrolyte leakage or evaporation, allowing electrodes to make electrical contact with power source as well as to enter and exit the housing, if needed, and also the ability to vent any unwanted gas generation, if needed.

The foregoing refers to polymeric actuators. In an exemplary embodiment these polymer actuators are formed from ion or pH responsive epoxy polymer Hydrogel based polymers. Examples of such polymers are described in commonly owned WIPO patent application WO 2008079440A2, Entitled 'SUPER ELASTIC EPDXY HYDROGEL", filed on Jul. 10, 2007 and published on Jul. 3, 2008. Other polymer actuator examples may contain polymers which have ionic functional groups, such as carboxylic acid, phosphoric acid, sulfonic acid, primary amine, secondary amine, tertiary amine, and ammonium, acrylic acid, methacrylic acid, vinylacetic acid, maleic acid, meta kurir yl oxy ethylphosphoric acid, vinylsulfonic acid, styrene sulfonic acid, vinylpyridine, vinylaniline, vinylimidazole, aminoethyl acrylate, methylamino ethyl acrylate, dimethylamino ethyl acrylate, ethylamino ethyl acrylate, ethyl methylamino ethyl acrylate, diethylamino ethyl acrylate, aminoethyl methacrylate, methylamino ethyl methacrylate, dimethylaminoethyl methacrylate, ethylamino ethyl methacrylate, ethyl methylamino ethyl methacrylate, diethylamino ethyl methacrylate, aminopropyl acrylate, methylaminopropyl acrylate, dimethylamino propylacrylate, ethylaminopropyl acrylate, ethyl methylaminopropyl acrylate, diethylamino propylacrylate, aminopropyl methacrylate, methylaminopropyl methacrylate, dimethylaminopropyl methacrylate, ethylaminopropyl methacrylate, ethyl methylaminopropyl methacrylate, polymers, such as diethylamino propyl methacrylate, dimethylaminoethyl acrylamide, dimethylaminopropylacrylamide, and alpha kurir yl oxy ethyl trimethylammonium salts, are reported to be of use but these examples are for reference and not intended to limit the scope or use of the invention.

An exemplary embodiment of a system 100 according to the present invention is schematically depicted with respect to FIG. 1A. System 100 includes power supply 101 coupled to controller 103 and an electrode set 104 within actuator assembly 105. Power supply 101 is configured to deliver current or pass charge between the electrodes set 104 under control of controller 103.

Actuator assembly 105 includes a polymeric actuator 102 and an associated electrode set 104 including top electrode 106 and bottom electrode 108. The electrode set 104 and the polymeric actuator 102 are contained within housing 110. Contained within housing 110 is an electrolyte solution 112U and 112L that immerses the electrode set 104 and actuator 102. Separating electrode 108 from electrode 106 is a porous separator membrane 114. The electrolyte includes an upper electrolyte portion 112U that is in fluidic and electrical contact with upper electrode 106 and polymeric actuator 102. The electrolyte also includes a lower electrolyte portion 112L that is in contact with the lower electrode 108. When power supply 101 passes current through electrode set 104, this results in a pH difference between upper electrolyte portion 112U and lower electrolyte portion 112L and more importantly modulates the pH of upper electrolyte portion 112U that is in contact with polymeric actuator 102. In one embodiment of FIG. 1A the upper electrode 106 is not in contact with polymeric actuator 102 and is responsive to power supply 101 to modulate the pH of upper electrolyte portion 112U. In a second embodiment of FIG. 1A upper electrode 106 is in direct contact with polymeric actuator 102. In a third embodiment, upper electrode 106 has a portion that extends into the polymeric actuator 106. This may be similar to an electrode discussed with respect to FIG. 3.

Polymeric actuator 102 is pH responsive and expands or contracts in response to a pH change in the upper electrolyte portion 112U. There are two types of polymeric actuators 102 that may be used including an "acid-responsive" polymeric actuator and a "base-responsive" polymeric actuator. An "acid responsive" polymeric actuator will expand in response to a decreased pH in upper electrolyte portion 112U surrounding polymeric actuator 102. This can be accomplished by providing a positive bias of electrode 106 relative to electrode 108. Applying the positive bias causes current to flow from electrode 106 to electrode 108 and causes a positive ion concentration in the upper electrolyte portion 112U surrounding actuator 102 to increase. Thus the upper electrolyte portion 112U surrounding actuator 102 becomes acidic (lower pH) and causes actuator 102 to expand. If the bias is reversed the upper electrolyte portion 112U surrounding actuator 102 becomes more basic which causes an opposite effect on actuator 102.

A "base responsive" polymeric actuator 102 also may be used. In that case, applying a negative bias to electrode 106 relative to electrode 108 will cause the pH in the upper electrolyte portion 112U surrounding polymeric actuator to increase which will in turn cause the base responsive polymeric actuator 102 to expand. When polymeric actuator 102 expands, it causes the entire actuator assembly 105 to expand.

Figure 1B:
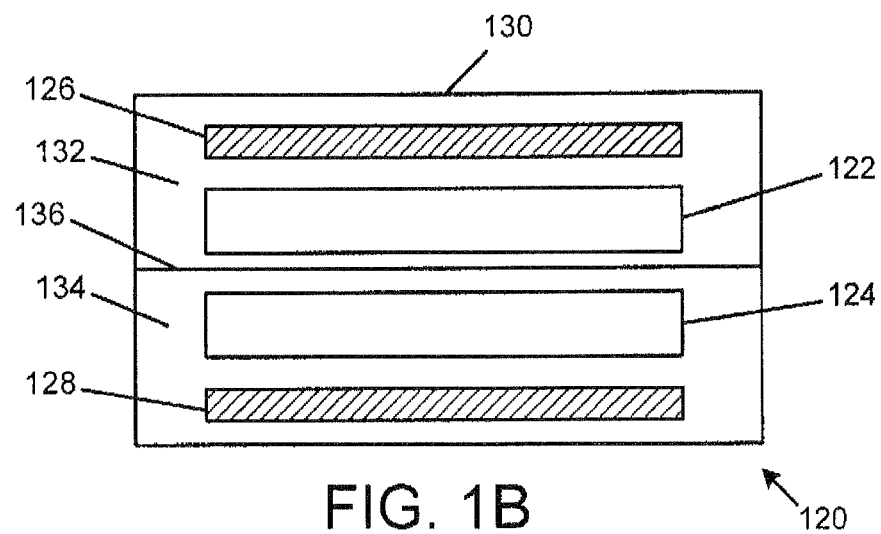
FIG. 1B depicts an exemplary actuator assembly 120.

An alternative design of an actuator assembly 120 utilizing both acid responsive and base responsive actuators is depicted in FIG. 1B in schematic form. Actuator assembly 120 includes an acid responsive polymeric actuator 122, a base responsive polymeric actuator 124, a top electrode 126, and a bottom electrode 128 all within housing 130. A top electrolyte 132 surrounds top electrode 126 and acid responsive actuator 122; a bottom electrolyte surrounds bottom electrode 128 and base responsive actuator 124. A porous separator membrane 136 separates the top electrolyte 132 from the bottom electrolyte 134.

When a positive bias current is applied between top electrode 126 and bottom electrode 128 and pH of the top electrolyte 132 decreases while the pH of the bottom electrolyte 134 increases. The decreased pH (acidity increase) of the top electrolyte 132 causes acid responsive polymeric actuator 122 to expand while the increased pH (more basic) of bottom electrolyte 143 causes base responsive polymeric actuator 124 to expand. Having two layers of actuators may double the total displacement obtainable for the actuator assembly 120. It is anticipated that additional layers of polymeric actuators with alternating layers of acid responsive and base responsive polymeric actuators can be used to further increase the maximum expansion of actuator assembly 120.

Figure 1C:
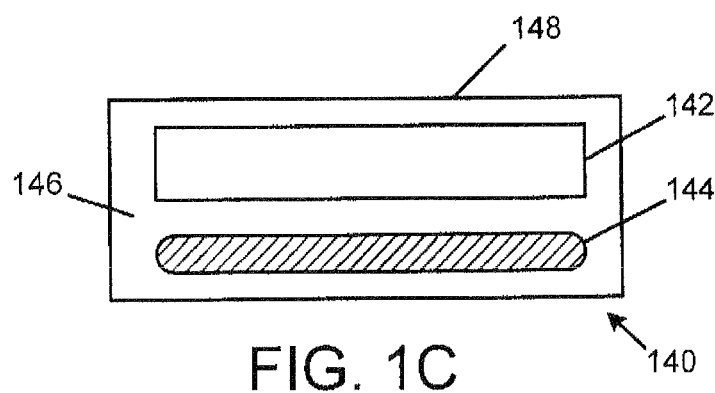
FIG. 1C depicts an exemplary actuator assembly 140.

An alternative embodiment of an actuator assembly 140 is depicted with respect to FIG. 1C and includes a pH responsive polymeric actuator 142, a container of pH modifying solution 144, and an electrolyte 146 all inside housing 148. When the container 144 is pierced or otherwise opened, it spills into electrolyte 146, modifying the pH of electrolyte 146. The changing pH within electrolyte 146 cause actuator 142 to expand or contract which in turn causes actuator assembly 140 to expand or contract.

In one embodiment actuator 142 is an acid responsive polymeric actuator and container 144 is a breakable container that contains an acidic solution. Upon breaking open container 144, the acidic solution lowers the pH of electrolyte 146 causing actuator 142 to expand. When actuator 142 expands, it in turn causes housing 148 to expand.

In another embodiment actuator 142 is a basic responsive polymeric actuator and container 144 is a breakable container that contains a basic solution. Upon breaking open container 144, the basic solution raises the pH of electrolyte 146 causing actuator 142 to expand. When actuator 142 expands, it in turn causes housing 248 to expand.

Another actuator 2 of the present invention with various details left out is depicted in plan view with respect to FIG. 2A. Actuator 2 includes a carrier 4 and a plurality of discrete polymeric actuators 6. The polymeric actuators 6 are disposed in an area arrangement (or a two-dimensional arrangement) across an upper surface of carrier 4. In an exemplary embodiment upper surface 8 is a planar surface 8 disposed along mutually perpendicular axes 10A and 10B.

The actuator 2 is further depicted with respect to FIG. 2B which is a cross section taken along AA of FIG. 2A. Each of the polymeric actuators 6 may be referred to as a polymeric pillar 6 that has a long axis extending along an axis 10C. In an exemplary embodiment axis 10C is mutually perpendicular to axes 10A and 10B.

Carrier 2 has a plurality of wells or holes 12 formed therein that define openings 14 along surface 8 of carrier 2. Each of the wells 12 supports one of the discrete polymeric actuators 6. In the illustrated embodiment each discrete polymeric actuator 6 has a volume that is primarily contained within a well 12. A small portion 16 of the volume of each polymeric actuator 6 may extend above the well 12.

Each of the discrete polymeric actuators 6 is formed from a material that is volumetrically responsive to a change in pH within an electrolyte 22 that is in contact with discrete polymeric actuators 6. Stated another way, when the electrolyte 22 changes pH, the volume of each discrete polymeric actuator 6 also changes. To cause this change in pH, actuator 2 includes an apparatus for changing the pH of the electrolyte 22.

In the depicted embodiment, the apparatus for changing the pH includes an electrode set which includes an upper electrode 18, a lower electrode 20, and a porous separator membrane 24 that separates electrode 20 from the electrolyte solution 22 in contact with polymeric actuators 6. Applying a current between upper electrode 18 and lower electrode 20 causes an ionic concentration change in electrolyte 22 which is logarithmically related to the pH of electrolyte 22.

In one embodiment, the discrete polymer actuators 6 are formed from an "acid responsive" polymer that expands in response to a decrease in pH of the surrounding electrolyte 22. By providing a positive bias at electrode 18 relative to electrode 20, the pH in surrounding electrolyte 22 decreases causing discrete polymeric actuators 6 to expand. To improve contact between polymeric actuators 6 and electrolyte solution 22, carrier 22 is formed from a "micro porous polymeric material" such as porous polyethylene.

The polymeric actuators are constrained such that when they expand, they tend to generate a net force and displacement primarily along axis 10C. Because most of the volume of each actuator 6 is contained within a well 12, the net expansion must be in an upward direction within each well 12. Further, the actuators 6 are packed together closely enough to constrain a "mushrooming" effect of the actuators 6 above the surface 8 to further enhance the net upward motion and force generated by actuators 6 during expansion.

The actuator assembly 2 includes a housing 26 that includes an upper portion 26A, lower portion 26B, and a compliant portion 26C. When the actuators 6 push upward they have the effect of expanding housing 26 along the axis 10C in response to the change in pH. In one embodiment actuator electrode 18 is rigid and functions as a rigid platen. Actuators 6 may push against electrode 18 that in turn pushes up against top portion 26A.

Figure 3:
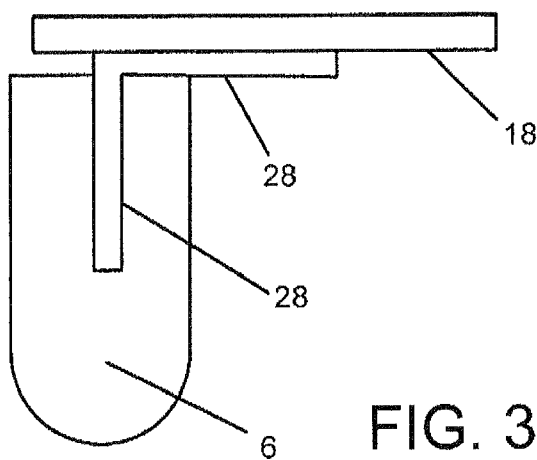
FIG. 3 depicts a detailed view of a single discrete polymeric actuator 6 from FIG. 2B having an individual electrode passing into the volume of actuator 6.

FIG. 3 depicts a preferred embodiment of the present invention wherein the electrode 18 contacts an individual electrode 28 that extends into the volume of polymeric actuator 6. This has an advantage of increasing the rate of expansion of the actuator material 6 by reducing a diffusion time of charge into polymeric actuators 6.

Figures 4A, 4B:
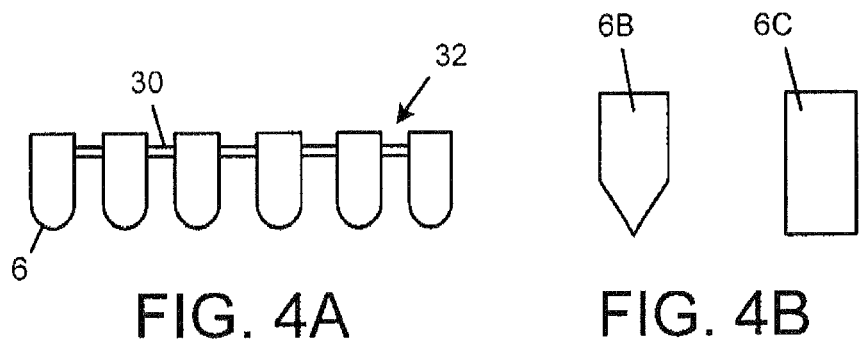
FIG. 4A depicts a plurality of discrete polymeric actuators 6 joined by a strip or web of polymeric material 30.
FIG. 4B depicts alternative shapes for discrete polymeric actuators.

FIG. 4A depicts an alternative embodiment for discrete polymeric actuators 6. FIGS. 2A and 2B depict polymeric actuators 6 as being completely separate. In an alternative embodiment, discrete polymeric actuators 6 are coupled together via a web of material 30. This has a the advantage of allowing the actuators to be molded or formed together as one part 32 that can be more easily or quickly assembled onto a carrier 4.

FIG. 4B depicts alternative shapes for polymeric actuators. FIGS. 2A, 2B, 3 and 4A depict polymeric actuators as having a cylindrical shape with a rounded lower end. In contrast, discrete polymeric actuator 6B has a cone shaped lower end and discrete polymeric actuator 6C is a cylindrical shape that is flat on both ends.

Figure 5:
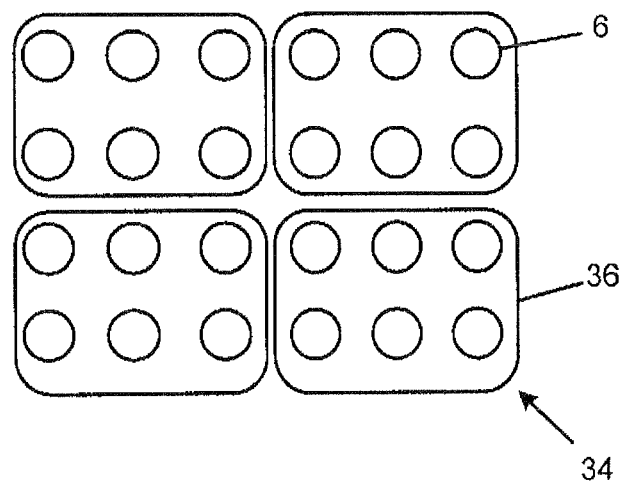
FIG. 5 depicts an actuator assembly using a plurality of carriers 36 rather than one single carrier 4 for supporting discrete polymeric actuators 6.

FIG. 2A depicts actuator assembly 2 as having a single carrier 4 holding discrete polymeric actuators 6. FIG. 5 depicts an alternative actuator assembly design 34 having multiple carriers 36.

FIGS. 6A and 6B depict an alternative actuator assembly 38 including a carrier 40 having individually addressable electrodes 42. FIG. 6B depicts a cross section taken through AA of FIG. 6A. Each electrode 42 is positioned to modulate the pH in an electrolyte 45 that is in the vicinity of each discrete polymeric actuator 44. The expansion of each polymeric actuator 44 is somewhat separately controllable via a corresponding contact 42 on carrier 40.

Actuator assembly 38 also includes an outer housing 46 upon which is formed a lower electrode 48. A portion 41 of carrier 40 abuts and seals against the housing 46 such that carrier 40 functions as a porous separator to separate lower electrode 48 from electrolyte 45 that surrounds polymeric actuators 44. A positive bias of an electrode 42 with respect to lower electrode 48 will tend to lower the pH within the electrolyte 45 that is adjacent to the lower electrode 48. In the case of acid responsive polymeric actuators 44 the volume of each discrete polymeric actuator 44 will tend to increase with the application of a positive bias to its corresponding or adjacent electrode 42. Except for the formation of electrode 48, the outer housing 46 is similar in construction to housing 26 described with respect to FIGS. 2A and 2B.

Figure 7A:
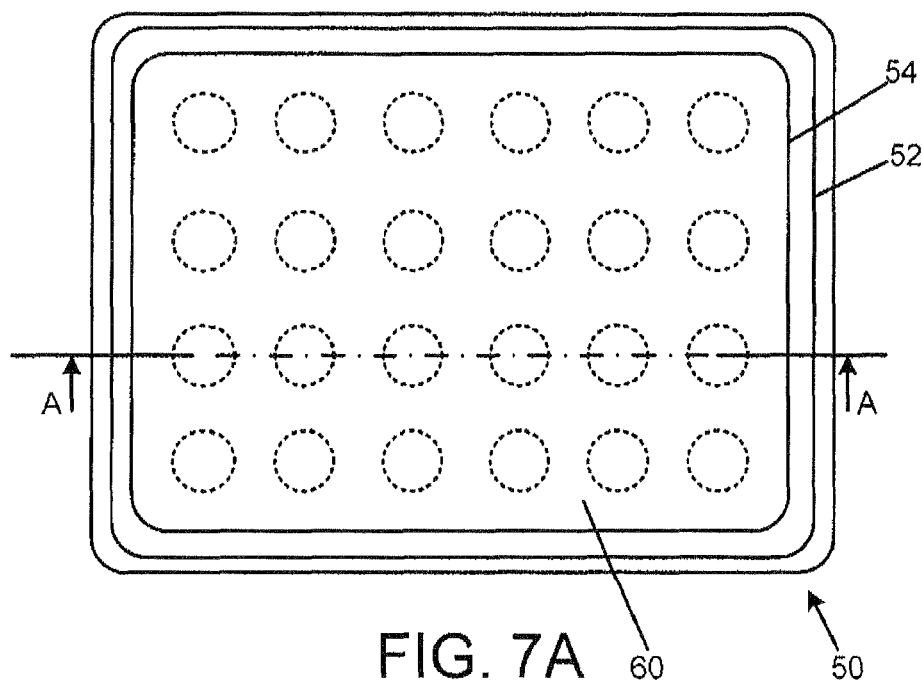
FIG. 7A depicts an alternative actuator assembly 50 including an electrode 60 formed on an upper surface of a polymeric web 56 that joins a plurality of discrete polymeric actuators 54.
Figure 7B:
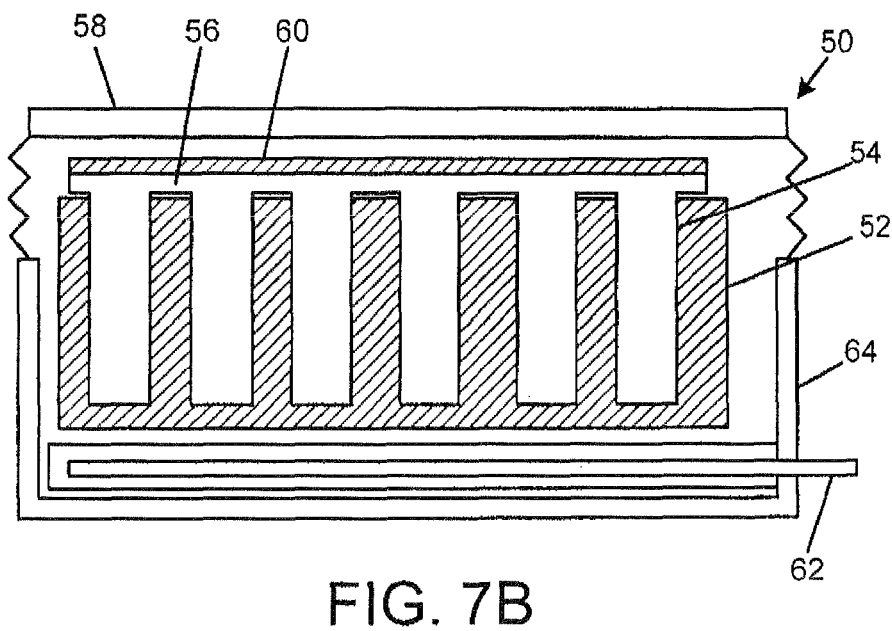
FIG. 7B depicts a cross section taken through assembly 50 along AA of FIG. 7A.

FIGS. 7A and 7B depict an alternative actuator assembly 50 including a carrier 52 and discrete polymeric actuators 54. FIG. 7B depicts a cross section taken through AA of FIG. 7A. Discrete polymeric actuators 54 are joined by a web 56 of polymeric material that defines an upper surface 58 common to a plurality of the discrete polymeric actuators 54. Disposed upon the upper surface 58 is an upper electrode 60. Applying a bias between upper electrode 60 and lower electrode 62 enables a modulation of the volume of the discrete polymeric actuators 54. Surrounding the carrier 52 and discrete polymeric actuators 54 is an outer housing 64 that is of similar construction to outer housing 26 described with respect to FIGS. 2A and 2B.

FIGS. 8A and 8B depict an alternative actuator assembly 64. FIG. 8B depicts a cross section taken through AA of FIG. 8A. Actuator assembly 64 includes a carrier 66 having an upper surface 68 and an opposing lower surface 70. A plurality of acid reactive discrete polymeric actuators 72 are disposed in an area arrangement along upper surface 68. A plurality of base reactive discrete polymeric actuators 74 are disposed in an area arrangement along lower surface 70. A porous separator 75 separates an upper electrolyte 77 from a lower electrolyte 79.

When a positive bias is applied to upper electrode 76 relative to lower electrode 78 this has the effect of reducing pH in the vicinity of actuators 72 and increasing the pH in the vicinity of actuators 74. Therefore all of the actuators 72 and 74 will expand under this bias wherein electrode 76 has a positive bias with respect to electrode 78. This design has the advantage of increasing maximum displacement of actuator 64 relative to an axis of 80. Actuator assembly 64 includes an outer housing 82 that is similar to the outer housing 26 described with respect to FIGS. 2A and 2B.

Figure 9:
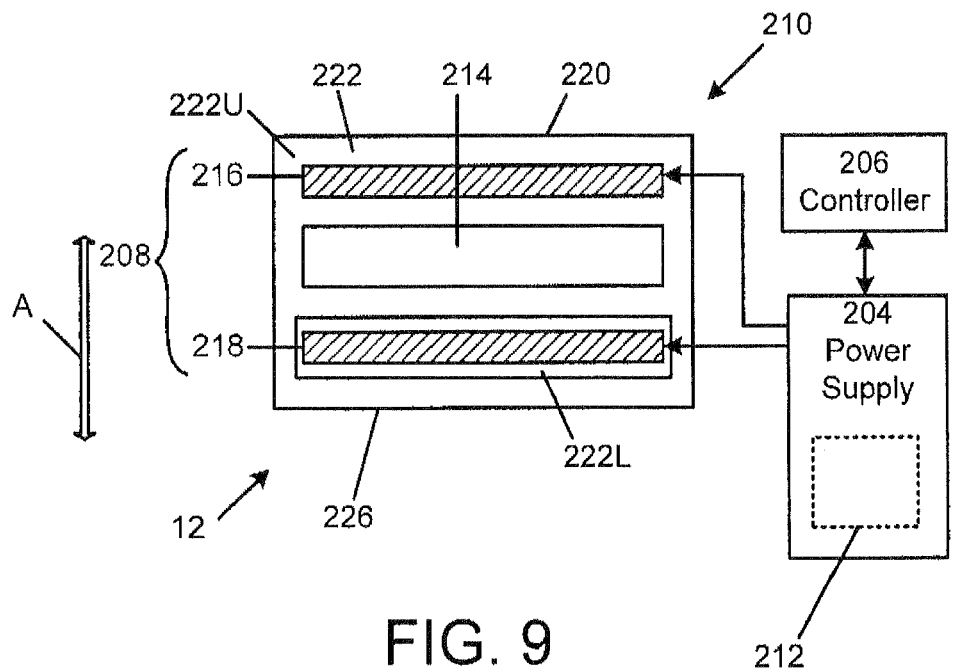
FIG. 9 depicts a polymeric actuator system in accordance with another aspect of the present invention.

An exemplary embodiment of a system 202 according to another aspect of the present invention is schematically depicted with respect to FIG. 9. System 202 includes power supply 204 couple to controller 206 and to electrode set 208 within actuator assembly 210. Power supply 204 is configured to deliver current or pass charge through the electrode set 208 under the control of controller 204. Controller 206 is configured to apply a current versus time profile to electrode set 208 by controlling power supply 204.

In other preferred embodiments controller 206 may be in communication with remote or wireless devices to allow for remote activation, deactivation and programming changes when needed. This may be done through IR (infrared), WIFI, RF (radio frequency), Magnetic or other types of wireless communication and would also allow for remote monitoring of an environment around system 202, and feedback from sensors monitoring performance and results of the activity of actuator 210.

In a preferred embodiment system 202 also includes a sensor 212 configured to sense characteristics within actuator 210 such as an electrical impedance within actuator 210. In an exemplary embodiment sensor 212 is integrated within power supply 204 and is configured to sense the electrical impedance between two electrodes of electrode set 208. In alternative embodiments sensor 212 may be separate from power supply 204. In additional alternative embodiments sensor 212 may sense parameters such as ion concentration, pH, complex impedance, resistance, resistivity, inductance, capacitance, and/or other measured parameters within actuator 210. Sensor 212 is configured to provide information to controller 206 that is indicative of the measured parameters. Controller 206 is configured to modify a current versus time profile to be applied to electrode set 208 in response to information received from sensor 212.

In a preferred embodiment actuator assembly 210 is configured to expand linearly along an axis A in response to charge that is passed between electrodes 216 and 218 of electrode set 208. Controller 208 receives information from sensor 212 that is indicative of the linear expansion of actuator assembly 210 that includes an impedance measured between electrodes 216 and 218. Controller 208 is configured to modify an amount of charge being passed between electrodes 216 and 218 in order to control the linear expansion of actuator assembly 210 to a predetermined value.

Actuator assembly 210 includes a polymeric actuator 214 and associated electrode set 208 including upper electrode 216 and lower electrode 218. The electrode set 208 and the polymeric actuator 214 are contained within housing 220. Contained within housing 220 is an electrolyte solution 222 that immerses actuator 214 and electrode set 208. Separating upper electrode 216 from lower electrode 218 is a porous separator membrane 226. The electrolyte includes an upper electrolyte portion 222U that is in fluidic and electrical contact with upper electrode 216 and polymeric actuator 214. The electrolyte 222 also includes a lower electrolyte portion 222L that is in fluidic and electrical contact with the lower electrode 218.

When power supply 204 passes current through electrode set 208, this results in an ionic concentration or pH difference between upper electrolyte portion 222U and lower electrolyte portion 222L and more importantly modulates the ionic concentration or pH of upper electrolyte portion 222U that is in contact with polymeric actuator 214. In one embodiment of FIG. 9 the upper electrode 216 is not in contact with polymeric actuator 214 and is responsive to power supply 204 to modulate the ionic concentration or pH of upper electrolyte portion 222U. In a second embodiment of FIG. 9 upper electrode 116 is in direct contact with polymeric actuator 214. In a third embodiment, upper electrode 216 has a portion that extends into or through the polymeric actuator 214. This may be similar to an electrode 288 discussed with respect to FIG. 12C.

Polymeric actuator 214 is pH responsive and will expand or contract in response to a pH change in the upper electrolyte portion 222U. Two types of polymeric actuators 214 that may be used include an "acid-responsive" polymeric actuator and a "base-responsive" polymeric actuator. An "acid-responsive" polymeric actuator will expand in response to a decreased pH in upper electrolyte portion 222U surrounding polymeric actuator 214. This can be accomplished by providing a positive bias of electrode 216 relative to electrode 218. Applying the positive bias causes current to flow from electrode 216 to electrode 218 and causes a positive ion concentration in the upper electrolyte portion 222U surrounding actuator 214 to increase. Thus the upper electrolyte portion 222U surrounding actuator 214 becomes acidic (lower pH) and causes actuator 214 to expand. If the bias is reversed the upper electrolyte portion 222U surrounding actuator 214 becomes more basic which causes an opposite effect on actuator 214.

A "base responsive" polymeric actuator 214 may also be used. In that case, applying a negative bias to electrode 216 relative to electrode 218 will cause the pH in the upper electrolyte portion 222U surrounding polymeric actuator to increase which will in turn cause the base responsive polymeric actuator 214 to expand. When the polymeric actuator 214 expands, it causes the entire actuator assembly 210 to expand.

Figure 10:
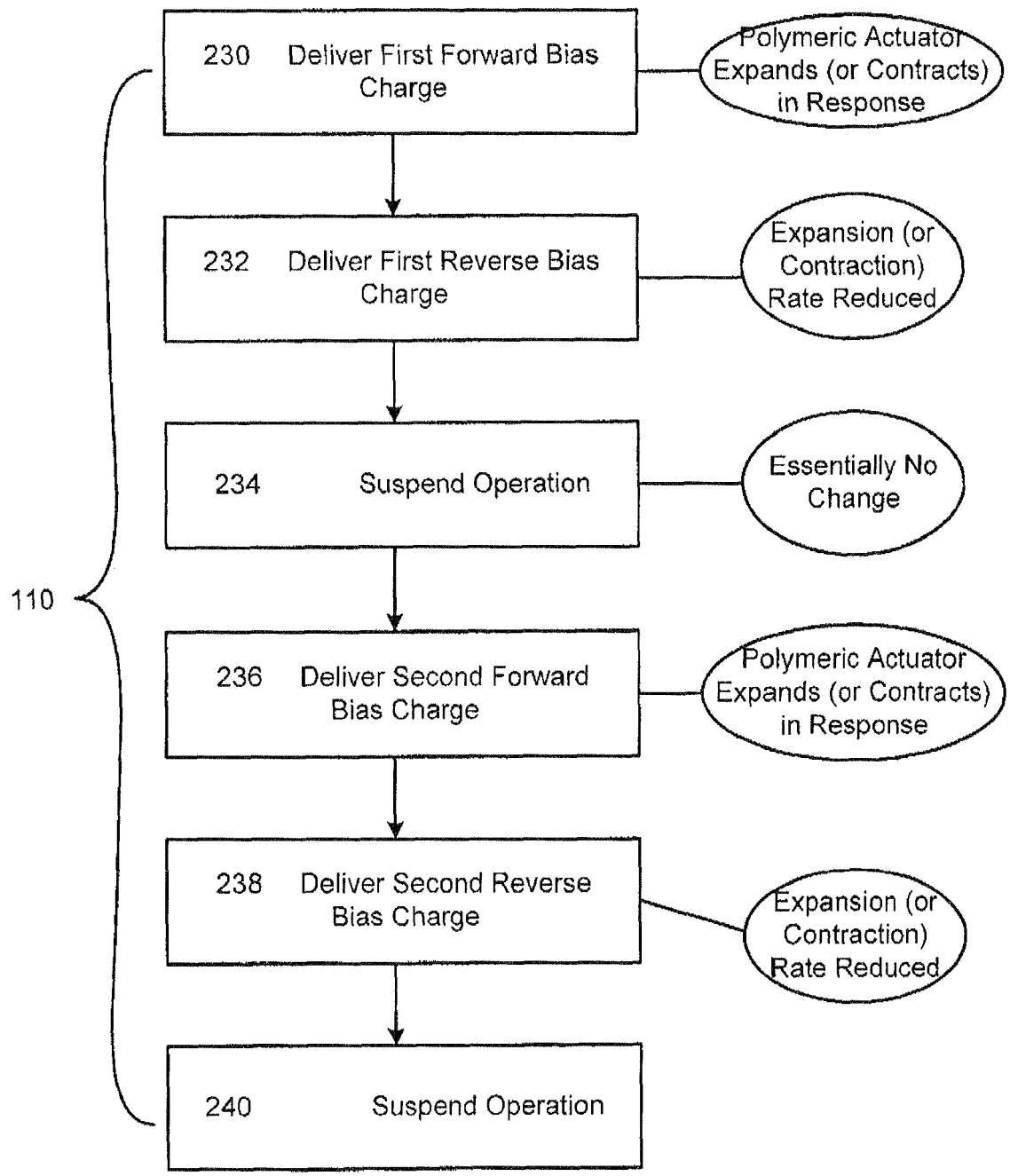
FIG. 10 depicts a method of the present invention in flow chart form.

An exemplary operation of actuator system 202 is depicted in flow chart form with respect to FIG. 10, Steps 230-238 represent steps of charge being transferred across electrode set 108 and/or of suspended operation by power supply 240 under the control of controller 206. While steps 230-238 are being performed, sensor 212 is providing information to controller 206 indicative of a linear expansive state of actuator assembly 210 along axis A. Controller 206 is responsive to the information and modifies the amount of charge being transferred between electrodes 216 and 218 in response to the information in order to provide a predetermined linear expanse state for actuator assembly 210 for each step of steps 230-238. At the beginning of the process of FIG. 10, polymeric actuator 214 has a first volume.

In step 230, power supply 204 deliveries a first forward bias charge between electrodes 216 and 218 during a first time period. This modifies the pH of the upper electrolyte 222U. Polymeric actuator 214 expands (or contracts) in response to the pH change from a first volume to a second volume. At the end of the first time period, the volume of polymeric actuator 214 is expanding (or contracting) at a first expansion (or contraction) rate. In a preferred embodiment, the power supply 204 adjusts a forward bias charge magnitude in response to information received from sensor 212 in order to achieve a predetermined second volume for polymeric actuator 214.

In step 232, power supply 204 delivers a first negative bias charge between electrodes 216 and 218 during a second time period. This oppositely changes the pH of upper electrolyte portion 222U relative to step 230 and primarily moves the pH toward a relatively neutral state. The polymeric actuator rate of expansion (or contraction) slows in response. In a preferred embodiment power supply 204 adjusts the negative bias charge magnitude in response to information from sensor 212 to reduce the magnitude of the rate of expansion to a magnitude that approaches zero as closely as possible. In one embodiment the rate of expansion is reduced to less than 50% of the first expansion rate. In other embodiments magnitude of the rate of expansion is reduced to less than 40%, less than 30%, less than 20%, less than 10%, less than 5%, or less than 1% of the first expansion rate. The magnitude of the first negative bias charge is less than the magnitude of the first positive bias charge since the negative bias charge is being used only to stop the volume change of actuator 214, whereas the first positive bias charge is being used to change the volume from a first volume to a predetermined second volume.

In step 234 power supply 204 suspends operation for a third time period during which the volume of actuator assembly 210 does not change significantly. In step 236 power supply 204 delivers a second forward bias charge between electrodes 216 and 218 during a fourth time period. Polymeric actuator expands (or contracts) from a third volume to a fourth volume in response to the delivery of the second forward bias charge. In a preferred embodiment, the third volume is equal to the second volume. Step 236 is similar to step 230 except that in an exemplary embodiment the amount of charge transferred in step 236 may be different than in step 230. This will be discussed in infra.

Step 238 is similar to step 232. During step 238, power supply 238 delivers a second reverse bias charge to electrode set 208 during a fifth time period to slow a magnitude of a rate of expansion (or contraction) of actuator 214. In step 240, operation of power supply power supply 204 is suspended during a sixth time period.

After step 240, the steps of applying forward bias charge (similar to steps 230 and 236) for expansion (or contraction), applying negative bias charge to slow or stop expansion (similar to steps 232 and 238), and suspending operation (similar to 234 and 240) may continue until actuator 214 reaches a maximum (or minimum) volume.

In an exemplary embodiment system 202 is configured to linearly expand actuator assembly 210 along an axis A in approximately equal sized steps. In this exemplary embodiment an apparatus similar to that depicted with respect to FIGS. 12A-12C (to be discussed infra) is utilized. In order to maintain equal size steps it is required that the forward bias charge transferred in step 236 be greater than that transferred in step 230. Subsequent steps will require yet larger amounts of charge transfer to achieve the same linear volume increase.

Figure 11:
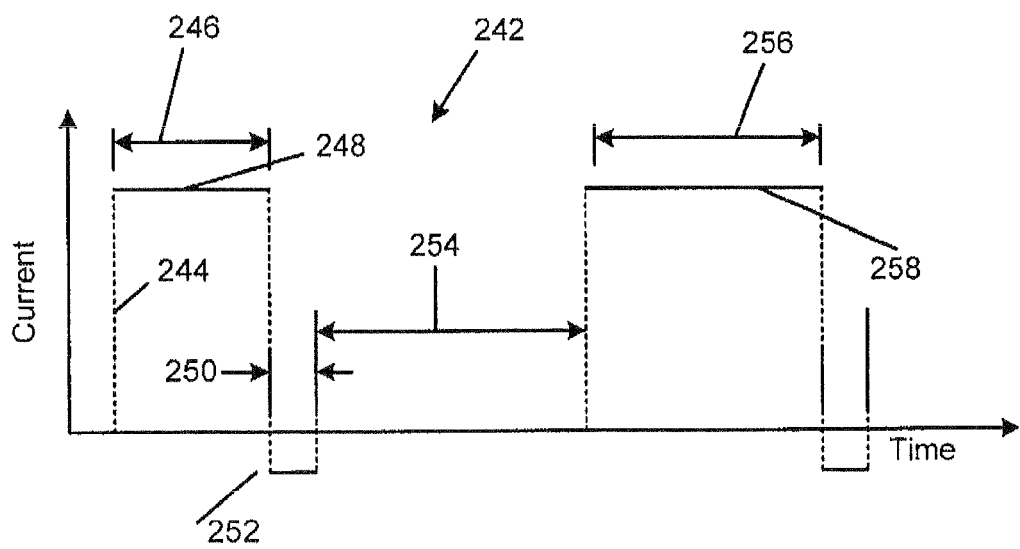
FIG. 11 depicts a current versus time curve of the present invention.

An exemplary graph of current versus time 242 delivered by power supply 204 to electrode set 208 is depicted with respect to FIG. 11. It is to be understood that current versus time 242 is delivered by power supply 204 under the control of controller 206. Controller 206 may be receiving inputs from a sensor 212 such as information indicative of an impedance between electrodes 216 and 218 (the impedance may also be measured from an additional third electrode if needed) and controller 206 may adjust a current level and or a current duration in response.

At an initial time 244 actuator 214 has an initial volume V. During a first time period 246 power supply 204 delivers a positive current level 248. This corresponds to step 230 of FIG. 10.

During a second time period 250, power supply 204 delivers a negative current level 252. Second time period 250 is of lesser magnitude than first time period 246. Second time period 250 may correspond to step 232 of FIG. 10. During a third time period 254, power supply 204 suspends operation. In some embodiments it may be desirable in the third time period to apply a positive current of smaller magnitude than level 248 instead of suspending operation entirely. Third time period 254 may correspond to step 234 of FIG. 10.

During a fourth time period 256 power supply 204 delivers a positive current level 258. Fourth time period 256 may be of longer duration than first time period 246. Fourth time period 256 may correspond to step 236 of FIG. 10.

While FIG. 11 depicts essentially a steady state DC current being applied to electrode set during time periods 246, 250, and 256, this does not have to be the case. In one embodiment the current is pulsed during each time period 246, 250, and 256. In a second embodiment the current is ramped up and down during each time period 246, 250, and 256. In a third embodiment the current applied is in a curve such as an exponential curve during portions or all of time periods 246, 250, and 256. Other examples of current versus time are possible while achieving the claimed invention.

Another embodiment of the invention is similar to that depicted in FIGS. 10 and 11 except that steps 232 and 238 are eliminated. Thus, the power supply 204 alternates between supplying forward bias charge similar to step 230 and in suspending operation similar to step 234. In such an embodiment the expansion rate of polymeric actuator 214 will slowly continue to expand (or contract) at an exponentially decreasing rate during time periods of suspended operation of power supply 204.

While polymeric actuator 214 is depicted in FIG. 9 as being a single unitary polymeric actuator 214, it is to be understood that polymeric actuator 214 may include a plurality of discrete or separate polymeric actuators 214. An exemplary embodiment of an actuator assembly 262 utilizing a plurality of discrete polymeric actuators 266 is depicted with respect to FIGS. 12A-12C.

Figure 12A:
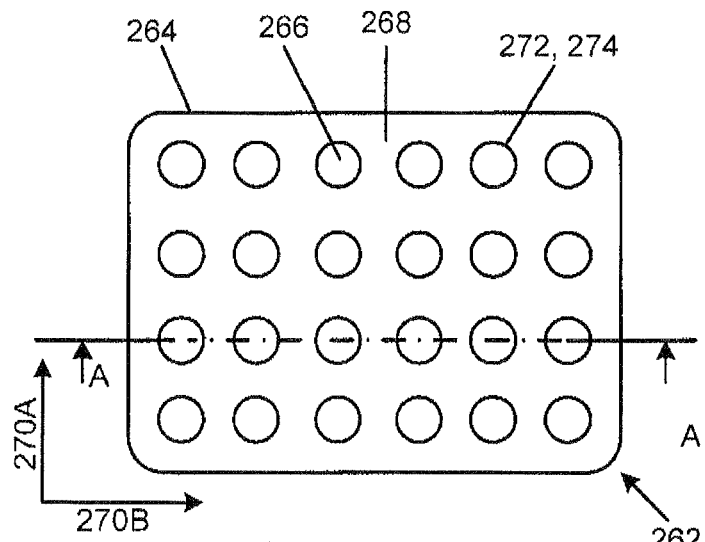
FIG. 12A depicts a plan or actuator view of an exemplary actuator assembly that can be utilized with the present invention.

An actuator 262 of the present invention with various details left out is depicted in plan view with respect to FIG. 12A. Actuator 262 includes a carrier 264 and a plurality of discrete polymeric actuators 266. The polymeric actuators 266 are disposed in an area arrangement (or a two-dimensional arrangement) across an upper surface 268 of carrier 264. In an exemplary embodiment upper surface 268 is a planar surface 268 disposed along mutually perpendicular axes 270A and 270B.

Figure 12B:
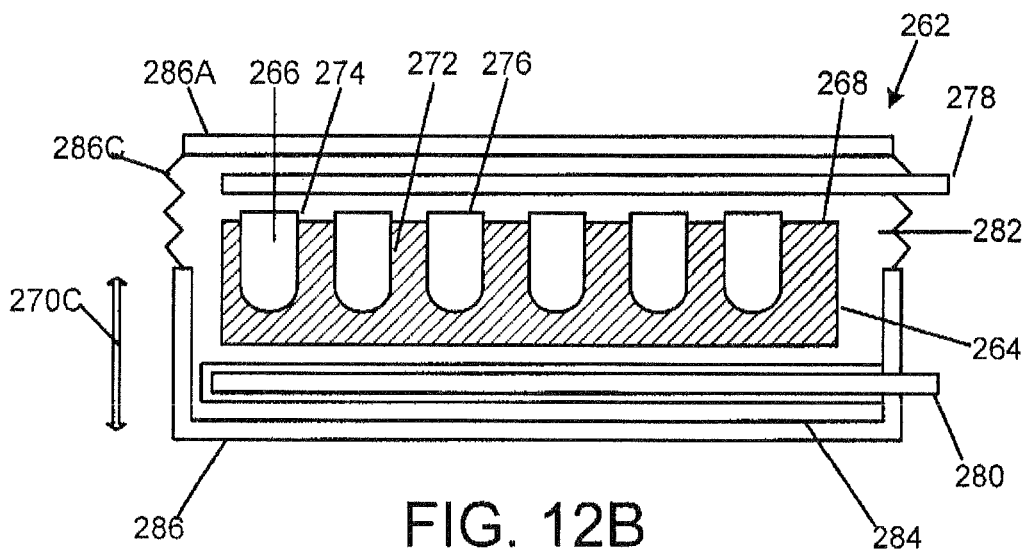
FIG. 12B depicts a cross section taken through the actuator along AA depicted in FIG. 12A.

The actuator 262 is further depicted with respect to FIG. 12B which is a cross section taken along AA of FIG. 12A. Each of the polymeric actuators 266 may be referred to as a polymeric pillar 266 that has a long axis extending along an axis 270C. In an exemplary embodiment axis 270C is mutually perpendicular to axes 270A and 270B.

Carrier 262 has a plurality of wells or holes 272 formed therein that define openings 274 along surface 268 of carrier 262. Each of the wells 272 supports one of the discrete polymeric actuators 266. In the illustrated embodiment each discrete polymeric actuator 266 has a volume that is primarily contained within a well 272. A small portion 276 of the volume of each polymeric actuator 266 may extend above the well 272.

Each of the discrete polymeric actuators 266 is formed form a material that is volumetrically responsive to a change in pH within an electrolyte 282 that is in contact with discrete polymeric actuators 206. Stated another way, when the electrolyte 282 changes pH, the volume of the each discrete polymeric actuator 266 also changes. To cause this change in pH, actuator 262 includes an electrode set 208 coupled to a power supply 204 (not shown in FIGS. 12A-12C) that is similar to that depicted with respect to FIG. 9.

The electrode set 208 includes an upper electrode 278 and a lower electrode 280. Actuator assembly 262 also includes a porous separator membrane 224 that separates electrode 280 from the electrolyte solution 282 in contact with polymeric actuators 266. Applying a current between upper electrode 278 and lower electrode 280 causes an ionic concentration change in electrolyte 282 which is logarithmically related to the pH of electrolyte 282.

In one embodiment, the discrete polymer actuators 266 are formed from an "acid responsive" polymer that expands in response to a decrease in pH of the surrounding electrolyte 282. By providing a positive bias at electrode 278 relative to electrode 280, the pH in surrounding electrolyte 282 decreases causing discrete polymeric actuators 266 to expand. To improve contact between polymeric actuators 266 and electrolyte solution 282, carrier 282 is formed from a "micro porous polymeric material" such as porous polyethylene.

The polymeric actuators are constrained such that when they expand, they tend to generate a net force and displacement primarily along axis 270C. Because most of the volume of each actuator 266 is contained within a well 272, the net expansion must be in an upward direction within each well 272. Further, the actuators 266 are packed together closely enough to constrain a "mushrooming" effect of the actuators 266 above the surface 268 to further enhance the net upward motion and force generated by actuators 266 during expansion.

The actuator assembly 262 includes a housing 286 that includes an upper portion 286A, lower portion 286B, and a compliant portion 286C. When the actuators 266 push upward they have the effect of expanding housing 286 along the axis 270C in response to the change in pH. In one embodiment actuator electrode 278 is rigid and functions as a rigid platen. Actuators 266 may push against electrode 278 that in turn pushes up against top portion 286A.

Figure 12C:
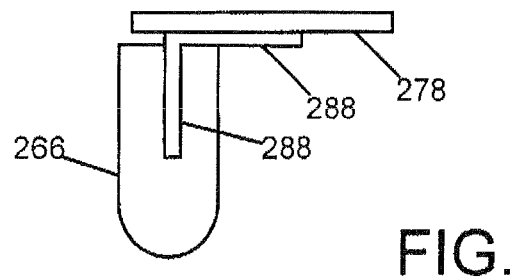
FIG. 12C depicts a detailed view of a single discrete polymeric actuator from FIG. 12B having an individual electrode passing into the volume of the actuator.

FIG. 12C depicts a preferred embodiment of the present invention wherein the electrode 278 contacts an individual electrode 288 that extends into the volume of polymeric actuator 266. This has an advantage of increasing the rate of expansion of the actuator material 266 by reducing a diffusion time of charge into polymeric actuators 266.

Other preferred embodiments may include multiple actuators 210 attached to a single controller 206 and power supply 204 with the electrodes 208 entering and exiting the exterior to continue on from first actuator package to the next actuator package to enable stacking or linear lines of actuators all in electrical connection.

Figure 13:
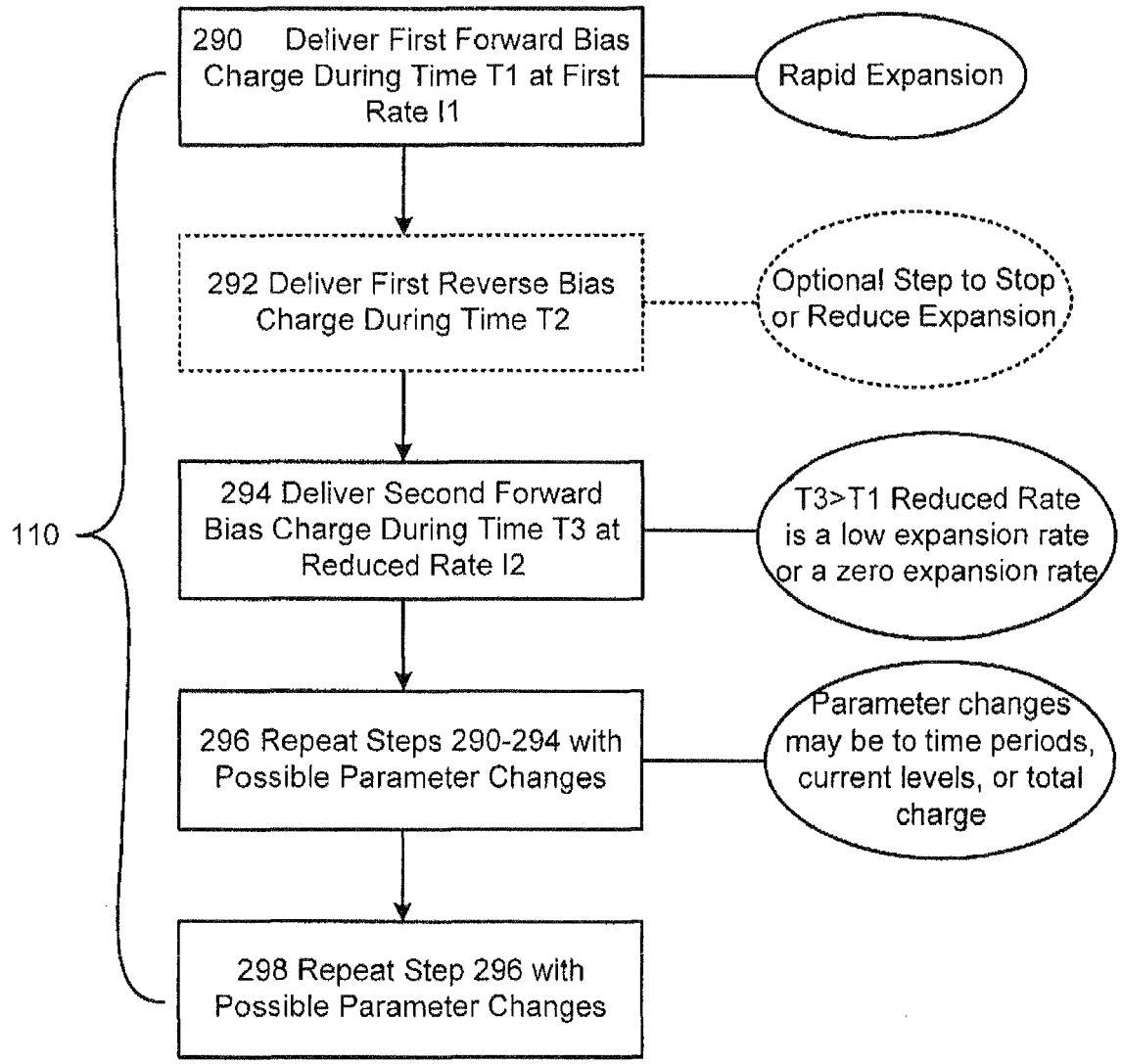
FIG. 13 depicts a method of the present invention in flow chart form.

FIG. 13 depicts an exemplary method of the current invention in flow chart form. This method may be used when actuator system 202 forms part of an IV pump for delivering medication to a patient. For example, actuator 210 may be utilized to compress an IV bag in a portable IV pump.

During the steps 292-298, power supply 204 is transferring charge between electrodes 216 and 218 under control of controller 206. Therefore controller 206 is executing the steps 292-298 utilizing power supply 204.

The pH of electrolyte 222U is modulated when current is passed between electrodes 216 and 218. For the purposes of FIG. 13 discussion we define a forward bias current as one which a pH change that results in an expansion of polymeric actuator 214. Therefore controller 206 modulates and determines the expansion of polymeric actuator according to a current versus time profile that is defined by steps 292-298.

Sensor 212 monitors the state of actuator assembly 210. Sensor 212 provides information to controller 206 that is indicative of an expansive state of polymeric actuator 214 and actuator assembly 210. Controller 206 is configured to modify operation in response to the information in order to control the expansion of actuator 210 to within a predetermined range.

The step 290, power supply 204 transfers a first forward bias charge Q1 between electrodes 216 and 218 during a time T1 and at an average rate I1. In response to the transfer of charge Q1, actuator 210 expands from a first volume to a second volume at a rapid rate due to a relatively high current level I1. During this expansion, a medication pump utilizing actuator system 202 may deliver a medication bolus roughly during time T1.

According to optional step 292, power supply 104 transfers a reverse bias charge during a time T2. During time T2, the rate of expansion is either reduced to a lower rate or is substantially halted.

According to step 294, power supply 204 transfers a second forward bias charge Q3 over a time T3 and at a current level I3. Current level I3 is lower than current level I1. Current level I3 may be less than 50% than current level I1. Time T3 is considerably longer than time T1. Time T3 may be more than ten times as long as time T1. In the case of a portable IV pump, the pump would be delivering a basal rate during time T3.

In step 296, steps of 290-294 are repeated (possibly including optional step 292) in which the parameters used may change. For example charge Q1 (the forward bias charge) may be increased in order to get the same size of bolus in the case of a portable IV pump. Step 298 is again a repeat of steps 290-294 in which parameters may change. Steps 298 can then be repeated again and again. In the embodiment in which system 202 is a portable IV pump this may continue until the pump has discharged all available fluid. Alternatively the actuator 214 may be returned to an initial state and then the method of FIG. 13 may be repeated.

Another aspect of the present invention is described below, with reference to FIGS. 14-19.

Critical high potency medications such as Schedule II pain therapeutics are often administered to patients at healthcare facilities. Schedule II pain medications are particularly important for patients having undergone surgeries or having conditions involving acute pain. In such a situation a doctor writes an order or prescription for treatment of the patient. The order is filled or verified by the facility pharmacy and may need to be renewed, e.g., every 48 to 96 hours. The order can then be dispensed by an automated cabinet system to a caregiver (e.g., a nurse) as required by the patient. The process flow for receiving and administering pain therapies according to a current process is depicted in FIG. 19A.

The situation according to FIG. 19A involves a patient that is experiencing severe pain and has been prescribed a Schedule II controlled substance pain medication such as morphine. In a first step 302, the caregiver assesses the patient's pain by computing a "pain score". Seeing that the patient needs pain therapy, the caregiver needs to obtain assistance from another caregiver in order to sign in to an automated dispensing cabinet system in a second step 304.

The caregiver must perform the steps according to steps 304-308 with a second caregiver as witness in order to assure proper handling and documentation for a Schedule II pain therapy medication. This is partly because such medications have been subject to substance abuse and theft.

In step 306, a glass cylinder of the medication is removed from the dispenser system. In the event that the full cylinder is not required in step 308, the caregiver loads a syringe and discards extra medication while the second caregiver observes and documents wastage medication. At this stage a computation of the correct dosage must often be calculated by the caregiver according to the concentration of the medication. Given the urgency of the situation and other distractions, errors can easily be made at this step that may result in a hazard to the patient and/or an insufficient dosage to eliminate the pain.

After the syringe is loaded the caregiver injects the medication into the patient at a step 310 and documents the dose given along with the pain score computation at a step 312. Disadvantages of this methodology include delays in administering the medication, potential errors, and issues with narcotic diversion. Additionally manual and time consuming patient-specific record keeping has to be completed and entered into the healthcare facility's information system on an ongoing basis further consuming the caregivers time.

Insufficient or delayed pain therapy may impair a patient's ability to heal and leave the healthcare facility. What is needed is a new process that addresses these issues while simplifying the process of administering the medication.

Figure 14A:
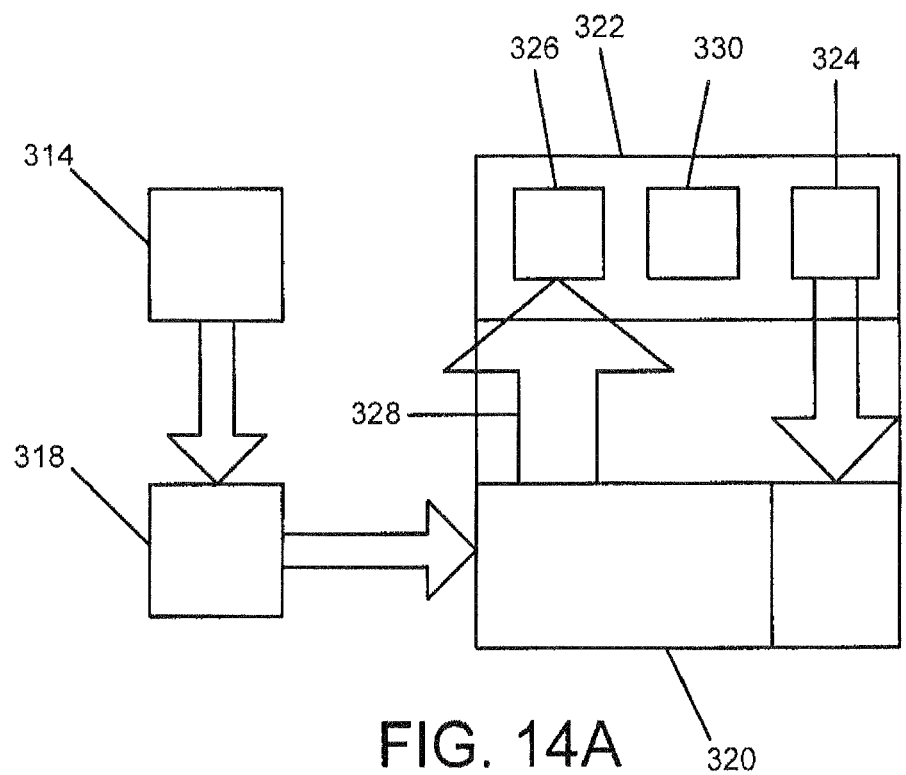
FIG. 14A depicts an overall system utilizing a further aspect of the present invention.
Figure 14B:
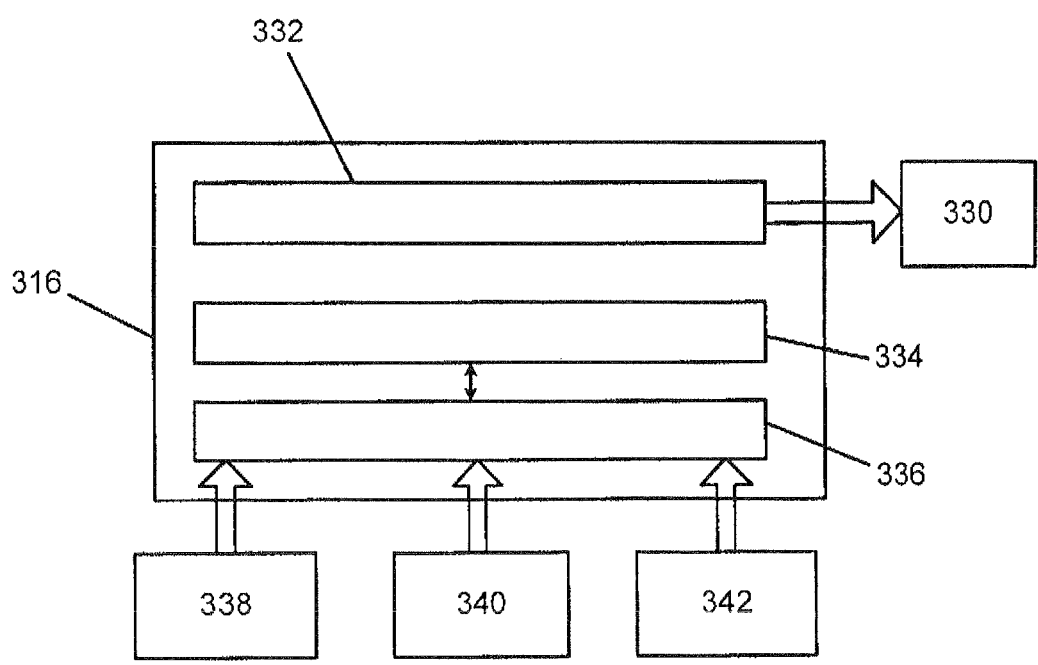
FIG. 14B depicts a simplified block diagram of a device according to the further aspect of the present invention.

A process flow and device of the present invention is depicted in FIGS. 14A and 14B respectively in block diagram form. The process starts at a device manufacturer or factory 314 at which medication delivery device 316 is manufactured. After manufacture, the device is delivered to a filling and programming facility 318 where it is filled with a high potency medication. After being filled the device is delivered to a pharmacy 320 that is part of a healthcare facility 322. Healthcare facility 322 is typically a hospital but it may also be a clinic, hospice, doctor's office, nursing center, ambulance, or other fixed or mobile healthcare facility where healthcare is provided to a patient.

At the healthcare facility 322 a doctor 324 may place an order for device 316. The pharmacy then makes the device available to a caregiver 326 via an automated dispensing system 328. The caregiver can then administer medication from device 316 to patient 330.

Device 316 is small and configured to be mounted to the body of patient 330. Device 316 includes therapeutic liquid 332 configured for delivery to patient 330. Device 316 includes a pump or actuator 334 under control of electronics 336 that controllably displaces the liquid 332 to the patient's body. The electronics 336 include programming instructions and parameters that govern the proper displacement of the liquid 332 to the patient 330.

The electronics 336 are configured to receive data or code inputs at different times during the process flow depicted in FIG. 14A. These inputs include an operating system 338 received at factory 314, medication and patient class-specific parameters 340 received at filling facility 318, and caregiver usage related inputs 342 during use in facility 322.

Figure 15:
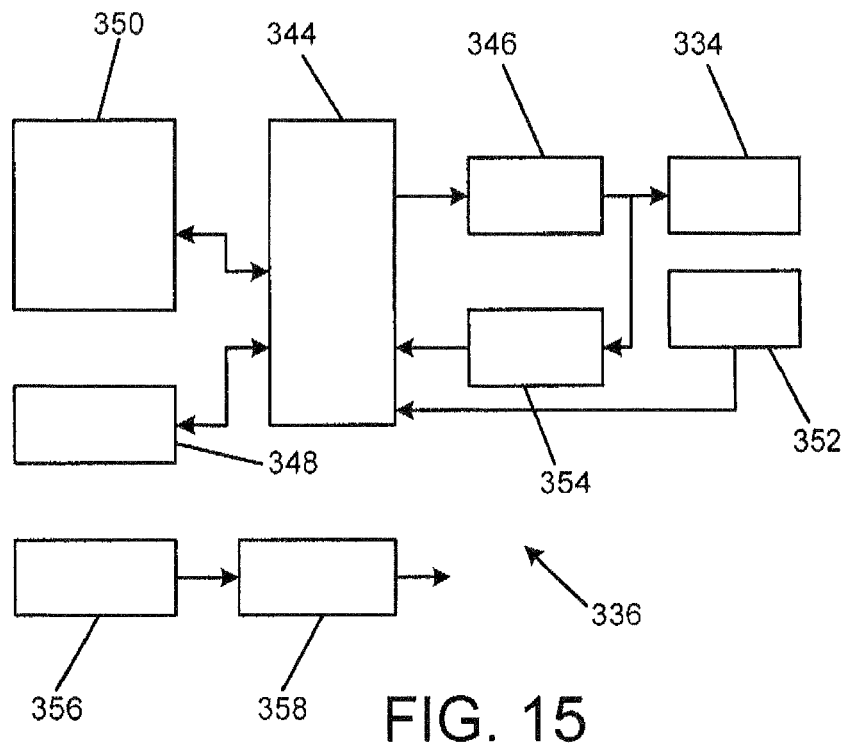
FIG. 15 depicts an electrical block diagram of a device according to the further aspect of the present invention.

The electronics 336 are described in greater detail in block diagram form in FIG. 15. A controller 344 which includes a processor, program memory, and data memory controls operation of actuator 334 via actuator driver 346. Controller 344 receives inputs from programming interface 348, user interface 350, sensor 352 and energy monitor 354.

Programming interface 348 is configured to receive inputs at factory 314 and filling facility 318. Programming interface 348 may include a wireless portion for receiving wireless inputs and/or a data connector. In one embodiment programming interface 348 is configured to receive portions or all of an operating system during the manufacture of device 316. Programming interface 348 is configured to receive parameters governing the operation of device 316 while device 336 is in filling and programming facility 318.

User interface 350 may include various features such as a display, buttons, LED indicator lights, audio indicators, as well as a wireless interface by which a caregiver can remotely make inputs. User interface 350 is configured to be utilized by caregiver 326. User interface 350 is generally not configured to alter the parameters received through programming interface 348 but generally only allows operation of device 316 within bounds provided by the parameters.

In an exemplary embodiment, electronics 336 include an energy monitor 354 that is configured to monitor current delivered by actuator driver 346 to actuator 334. In this embodiment actuator 334 includes a polymeric actuator that is configured to change volume and displace fluid from a liquid container or bag 332 in response to an amount of charge received from actuator driver 346. Information from energy monitor 354 is fed back to controller 344 to assure that a specified amount of charge is passed from actuator driver 346 to actuator 334. Other embodiments of device 316 can also be contemplated for moving fluid such as a pump that may require other forms of energy monitors.

Sensor 352 may be a pressure sensor configured to sense a pressure exerted on the therapeutic liquid by actuator 334. The sensed pressure may be used to control operation of actuator driver 346. The sensor can also be utilized as a secondary feedback path to provide redundant monitoring of the actuator for safety purposes. Other types of sensors 352 are contemplated to be used in device 316 such as displacement sensors, capacitive sensing, inductive sensing, to name a few.

Device 316 also includes a self contained power source or battery 356 that provides power to a voltage regulator 358. Voltage regulator 358 provides appropriate logic voltages to electronics 336.

Figure 16:
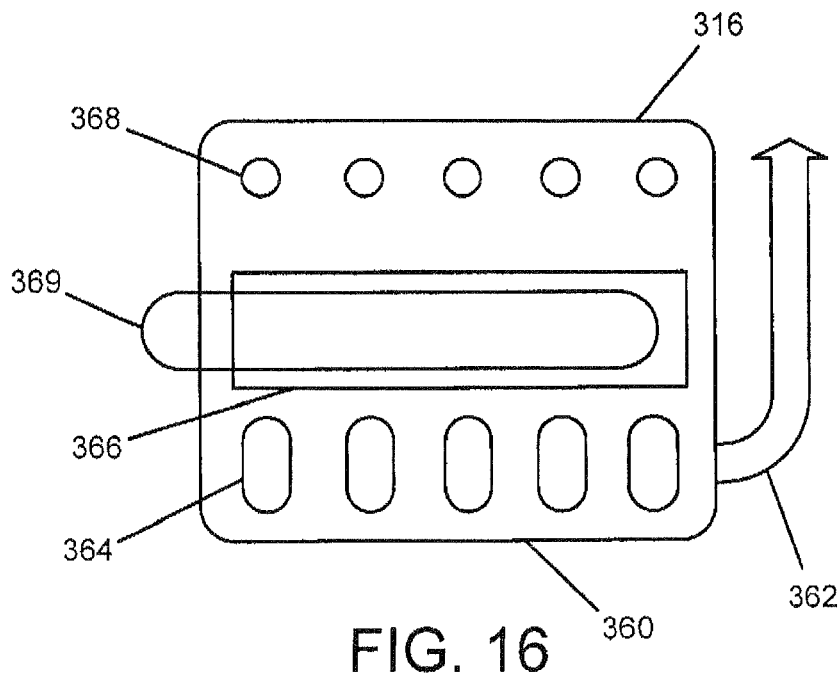
FIG. 16 depicts a simplified diagram of a device according to the further aspect of the present invention.

Device 316 is depicted in simplified schematic form in FIG. 16. Device 316 includes an outer housing 360 that is configured to be mounted to the body of patient 330. Once housing 360 is mounted on patient 330, a conduit 362 is coupled to the patient so that therapeutic liquid reservoir 332 is now coupled to patient 330. In a preferred embodiment the fluid coupling to the patient is subcutaneous. Alternatively, embodiments may have alternative modes of medication administration such as intravenous, intramuscular, trans-dermal, or other methods to enable a fluid to cross the skin barrier.

Device 316 includes a user interface 350 that may include any or all of keys 364, display 366, and an LED indicator 368. The user interface 350 may also include an external wireless device (not shown) that is configured to communicate with controller 336 using a wireless link such as RFID, IR, Bluetooth or other forms of wireless communication. The user interface may provide status and historical therapeutic and event information to the operator via wired or wireless methods.

Device 316 may also include a security measure or device configured to limit access to use of device 316. Various security measures may include physical keys or user interfaces requiring the caregiver 326 to enter a code to unlock or enable the device 316.

An example of a security measure includes a removable label 369 having a code that is utilized to unlock device 316 once the label is removed. This code may be entered by the pharmacist or caregiver for the purpose of activating device 316 and enabling medication to be administered by device 316. The label may be kept in a secured location such as upon a patient chart. Other examples of security measures include wireless devices that interface with device 316 and utilize a security code mechanism, proximity sensing mechanism or combination thereof.

Figure 17:
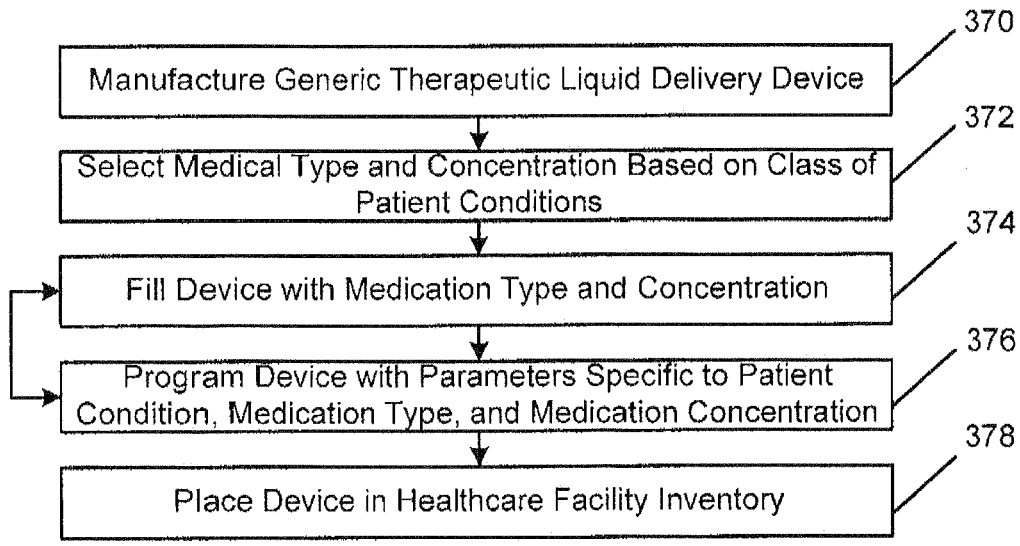
FIG. 17 depicts a method of manufacturing, configuring, and delivering a device such as one depicted according to FIGS. 14B, 15 and 16.

A method of providing device 316 to healthcare facility 322 caregivers is described with respect to FIG. 17 in flow chart form. In a first step 370, device 316 is manufactured in factory 314. As part of the manufacturing process, an operating system is installed onto controller 344. Device 316 is then transferred to filling and programming facility 314 in an unfilled state before or after step 372. At this point, device 316 may be used for a wide range of potential therapies.

According to 372, a medication type and concentration is selected based on a particular class of patient conditions from among a plurality of different classes of patient conditions. Based upon the particular class, device 316 is filled with the medication type and concentration in step 374. In step 376, parameters are stored on controller 344 that are specific to the (1) class of patient conditions, (2) the type of medication, and (3) the concentration of the medication. The parameters govern the operation of the device 316 according to safety and efficacy requirements of the particular type and concentration of the medication. Some examples of these parameters follow:

Bolus Dosage Selection: A selection or range of possible bolus dosages are provided consistent with the class of patient conditions, the medication type, and concentration. In one exemplary embodiment there is no limits on the dosages but there are "soft guardrails" wherein the device 316 is configured to issue warnings when a bolus dosage or sequence of dosages have values that are outside of a recommended range. The warning may be a visual and/or audible warning issued from user interface 350. The warning may include warning information that is transmitted wirelessly to another device such as a cellular phone or network, a computer network, a PDA, or any other device that can provide a warning to a caregiver.

Maximum Dosage Over Specified Time Periods: For example, there may be an upper limit on the total dosage that should be administered over 24 hours. In one embodiment the device 316 may be configured to issue a warning to the caregiver if the dosage over a specified time period is above a threshold.

Minimum Dosage Since the patient is of a certain patient class there may be a lower limit dosage below which is insufficient to reduce patient suffering and/or facilitate recovery. If a caregiver operates the device below the minimum, then a warning may be generated.

In one embodiment of the invention, step 374 is performed before step 372. In another embodiment, step 374 is performed after step 376. In yet another embodiment steps 374 and 376 are performed concurrently.

Once the device 316 has been filled and programmed according to steps 374 and 376, the device is placed in inventory of healthcare facility 322 in a step 378. According to steps 374 and 376, device 316 has been filled and programmed for a specific class of patient conditions. The parameters that are inputted according to step 376 cannot be overridden by a caregiver and are preferably stored in a write once or write protected memory in controller 336 to prevent any change to them.

Figure 18:
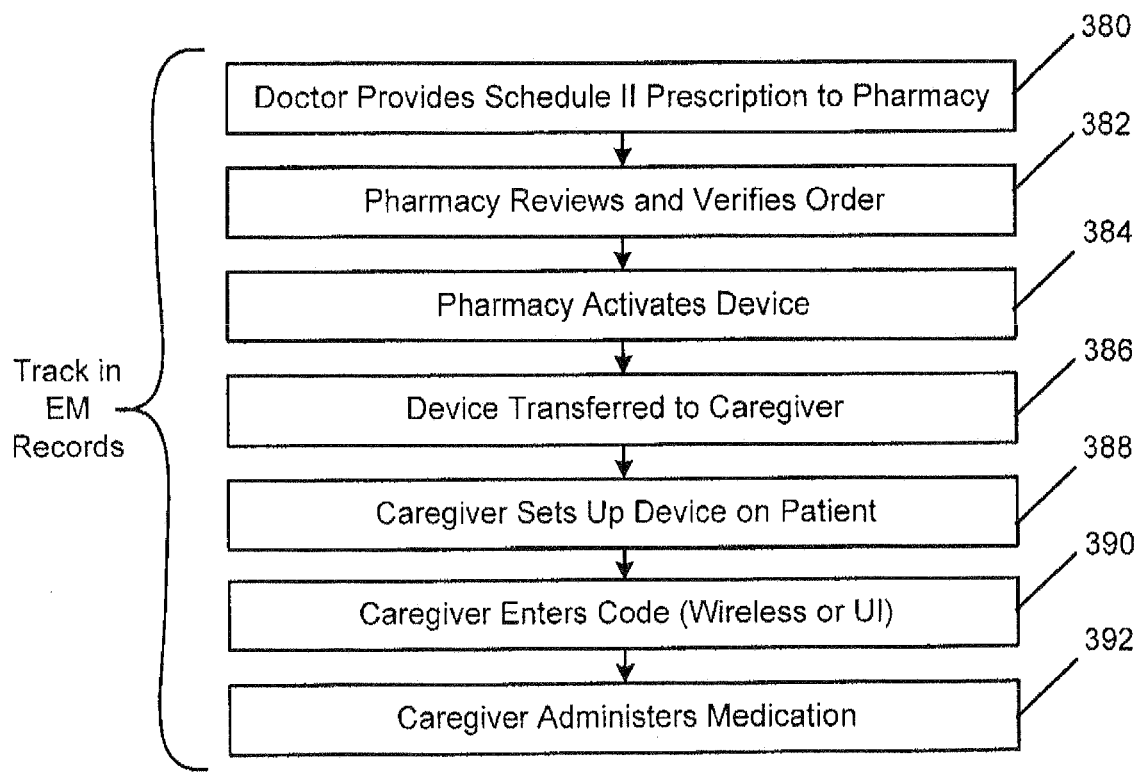
FIG. 18 depicts a method of use of a device provided according to the method FIG. 17.

A method of use of device 316 is depicted according to FIG. 18 in flow chart form. The discussion that follows will refer to a situation requiring pain medication but it is to be understood that a similar procedure may be used for other types of medications. Prior to step 380 the device 316 is in inventory in pharmacy 320. A doctor 324 may have a patient 313 (FIG. 14A) who is or will be experiencing considerable pain following an acute illness, surgical procedure, or bodily malfunction.

According to step 380, the doctor 324 produces a prescription for the pain medication which is transferred to pharmacy 320. A pharmacist reviews the prescription, selects device 316, and verifies the order according to step 382. The pharmacist will select a device 316 having that is pre-configured with parameters, medication type, and concentration that are consistent with the prescription.

Once the pharmacist has verified the proper device according to the order, the pharmacist activates the device 316 according to step 384. According to step 386 the pharmacist then utilizes an automated dispensing system to transfer the device to caregiver 326. The caregiver 326 then places upon the patient and couples the device via an administration route (conduit and coupling means) 362 to the patient 330 according to step 388. In an exemplary embodiment, administration route is subcutaneous. In step 390, the caregiver 326 enters a code into device 316 that unlocks the device and enables administration of medication to patient 330. In step 392 the caregiver manipulates the user interface 350 to administer the medication to patient 330.

The method of this invention has substantial benefits over the current methods of administration using syringes. This is illustrated by comparing FIGS. 19A and 19B that contrast the current prior art method (FIG. 19A) to the new process according to the present invention. As discussed before in the background, the current processes involving syringes includes steps 302-312 as illustrated in FIG. 19A. The new process is depicted in steps 402, 404, and 406. As before, the caregiver does assess patient pain and compute a pain score. According to the new method, the caregiver can then utilize user interface 350 to quickly unlock the device 316 and administer medication immediately as needed without help from another caregiver and without all the steps 302-312 of the prior art. Because device 316 has an internal memory, an automatic record is generated of the medication administration according to step 406 that can then be downloaded or accessed via wireless transmission and update the patient specific electronic records at the healthcare facility.

At this point several examples of pre-configured devices 316 will be disclosed. Each of these devices are initially the same design produced in factory 314 but become configured for a particular class of patients within filling within facility 318.

EXAMPLE 1

Morphine

According to this example of step 374 of FIG. 17, the device 316 is filled with morphine having a 50 mg/ml (milligrams of Morphine per milliliter) concentration. The device receives bolus dose parameters according to step 376 to enable a caregiver to provide boluses of 0.5 mg (0.01 ml), 1.0 mg (0.02 ml), 2.0 mg (0.04 ml), and 5.0 mg (0.1 ml).

EXAMPLE 2

Hydromorphone

According to this example of step 374 the device 316 is filled with hydromorphone having a 10 mg/ml concentration. In step 376 the device receives bolus dose parameters enabling the caregiver to provide doses of 0.2 mg (0.02 ml), 0.25 mg (0.025 ml), 0.5 mg (0.05 ml), 1 mg (0.1 ml), and 2 mg (0.02 ml).

EXAMPLE 3

Fentanyl

According to this example of step 374 the device 316 is filled with fentanyl having a concentration of 0.05 ml/mg. The device receives bolus dose parameters to enable the caregiver to inject boluses of 0.015 mg (0.3 ml), 0.025 mg (0.05 ml), 0.05 mg (0.1 ml), 0.075 mg (0.15 ml), and 0.1 mg (0.2 ml).

The present invention has been described as delivering Schedule II controlled substances for pain relief. However the present invention may deliver other fluids such as pharmaceutical drugs, other controlled substances, vitamins, hormones, hydration liquids, biologics, liquids with site specific identification or therapy molecular tags, insulin, immune system therapeutics such as Enbrel & Humira, and gene therapeutics. In addition other non-opioid medications may be used to supplement analgesia, including non-steroidal anti-inflammatory medications and low-dose anti-depressants.

Figure 20A:
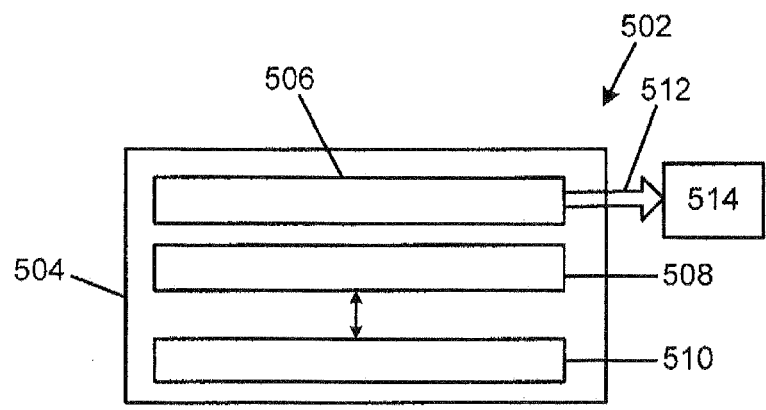
FIG. 20A depicts an exemplary medication delivery device of the present invention in block diagram form.
Figure 20B:
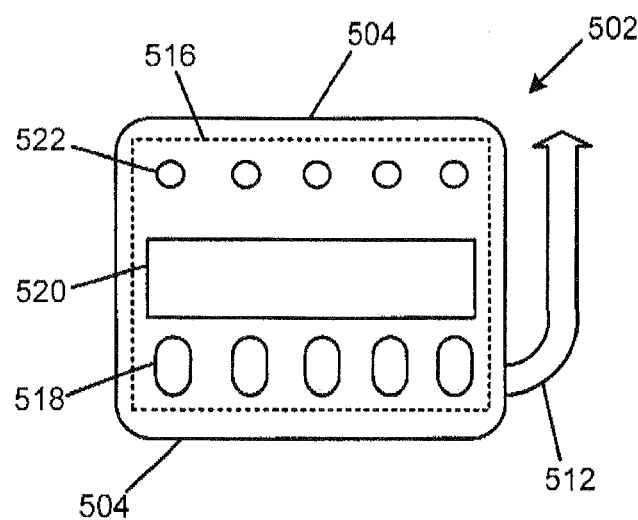
FIG. 20B depicts an exemplary medication delivery device of the present invention in schematic form.

Referring now to FIGS. 20A-26, an exemplary embodiment of a medication delivery apparatus 502 according to the present invention is depicted in block diagram form with respect to FIG. 20A and schematic form with respect to FIG. 20B. Medication delivery apparatus 502 includes an outer housing 504 configured to be attached or mounted to a patient body. Within housing 504 is a collapsible reservoir 506 adjacent to an area actuator assembly 508 that is electrically coupled to control and memory electronics 510.

Area actuator assembly 508 is responsive to electrical signals received from control electronics 510. Area actuator assembly 508 is configured to expand and press upon collapsible reservoir 506 in response to charge or current received from electronics 510. Area actuator 510 will be described in more detail with respect to FIG. 21 and later figures.

When area actuator assembly 508 expands and compresses collapsible reservoir 506, fluid within collapsible reservoir 506 is displaced under pressure from reservoir 506, through conduit 512, and to patient 514. In a preferred embodiment a subcutaneous fluid interface exists between conduit 512 and patient 514.

Disposed upon outer housing 504 is a user interface 516. User interface 516 may includes any or all of input keys or buttons 518, display 520, and LED indicator lights 522. User interface 516 may also include a wireless device (not shown) utilized to control medication delivery device 502, and facilitate access to electronic medical records stored in the device memory. The user interface is also configured to facilitate secure access to the device when necessary.

Figure 21:
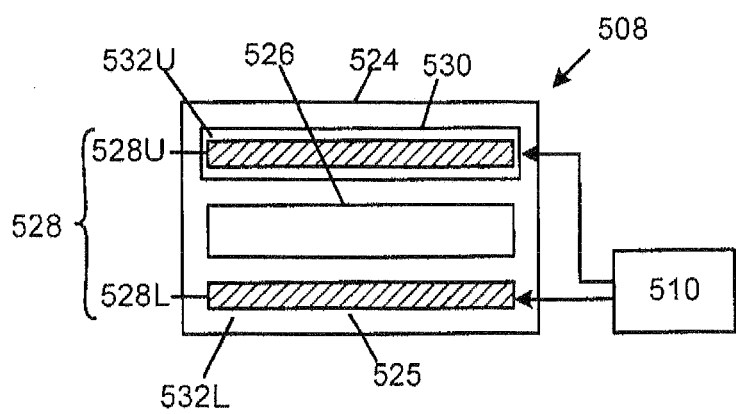
FIG. 21 depicts an actuator assembly utilized in the medication delivery device of the present invention.

FIG. 21 depicts a preferred embodiment of actuator assembly 508 coupled to electronics 510. Actuator assembly 508 is a sealed device including an outer housing 524 that may include a flexible film material to allow for expansion of housing 524. Outer housing 524 is sealed and encases a sealed region 525 that includes inner contents of actuator assembly 508.

Inner contents of actuator assembly 508 include a responsive material 526 disposed between electrodes 528 including upper electrode 528U and lower electrode 528L. A porous separator membrane 530 separates upper electrode 528U from sealed region 525. Also within sealed housing 524 is an electrolyte solution 532 including an upper electrolyte solution 532U that is between separator membrane 530 and upper electrode 528U and a lower electrolyte solution 532L that is between membrane 530 and housing 524.

In a preferred embodiment responsive material 526 is polymeric actuator 526 that is responsive to pH changes within lower electrolyte solution 532L. Electronics 510 are configured to pass charge between electrodes 528 and, in doing so, modulate the pH within the lower electrolyte 532L by changing the charge distribution within housing 524. There are two types of polymeric actuators 526 that may be used within actuator assembly 508 including an "acid-responsive" polymeric actuator and a "base-responsive" polymeric actuator. An "acid-responsive" polymeric actuator will expand in response to a decreased pH in electrolyte 532L surrounding polymeric actuator 526. This can be accomplished by providing a positive bias of electrode 528U relative to electrode 528L. Applying the positive bias causes current to flow from electrode 528U to electrode 528L and causes a positive ion concentration in the electrolyte 532L surrounding actuator 526 to increase. Thus the electrolyte 532L surrounding actuator 526 becomes acidic (lower pH) and causes actuator 526 to expand. (If the bias is reversed the electrolyte 532L surrounding actuator 526 becomes more basic which causes an opposite effect on actuator 526.)

A "base responsive" polymeric actuator may also be used. In that case, applying a negative bias to electrode 528L relative to electrode 528U will cause the pH in the electrolyte 532L surrounding polymeric actuator to increase which will in turn cause the base responsive polymeric actuator 526 to expand. When polymeric actuator 526 expands, it causes the entire actuator assembly 508 to expand.

Other designs of actuator assemblies 508 can be envisioned using multiple polymeric actuators 526 and more than two electrodes 528. These alternative designs may be of various geometric shapes and sizes and be substituted into the medication delivery device of the present invention without departing from the broad scope of the invention.

Figure 22A:
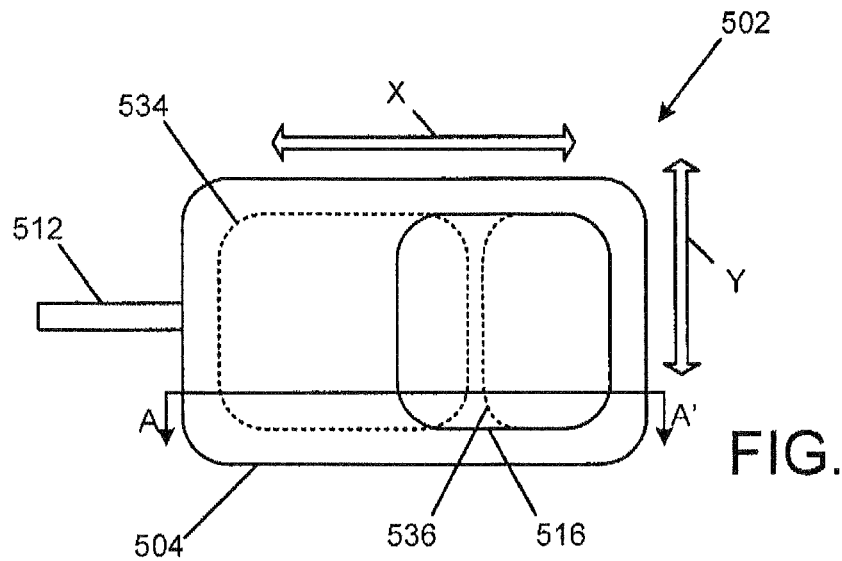
FIG. 22A depicts a plan view of a medication delivery device of the present invention.
Figure 22B:
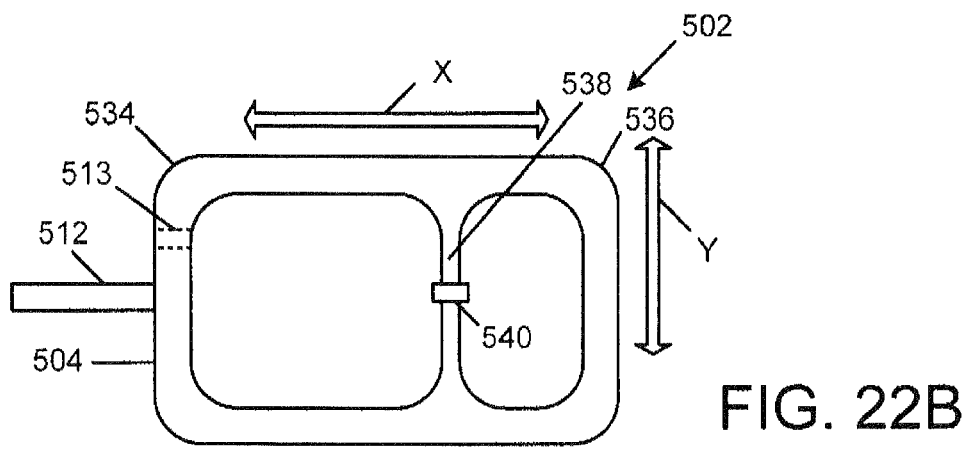
FIG. 22B depicts a cutaway plan view of a medication delivery device of the present invention to illustrate pockets for holding device components.
Figure 22C:
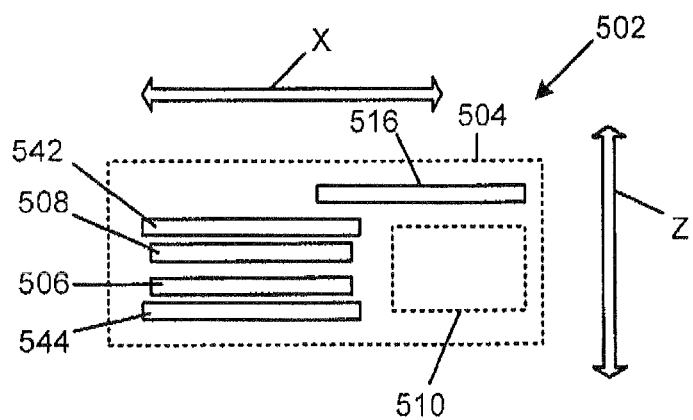
FIG. 22C depicts a cross-sectional view of a medication delivery device of the present invention.

A resulting medication delivery device 502 is in top plan view in FIG. 22A, cutaway view in FIG. 22B, and in cross section view in FIG. 22C. In FIG. 22A and in figures that follow certain details of device 502 are left out for illustrative simplicity. FIG. 22A depicts a top view of medication delivery device 502 illustrating outer housing 504, user interface 516, and fluid conduit 512. Device 502 has its longest dimension along a primary lateral axis X, a second longest dimension along secondary lateral axis Y, and the minimum dimension along depth axis Z (FIG. 22C). Axes X, Y, and Z are mutually orthogonal. Arranged along primary axis X are an actuator/reservoir pocket 534 and an electronics pocket 536. This arrangement minimizes a depth dimension of device 502. This is important for patient comfort, since patients are more sensitive to the thickness of a body carried device than to the lateral dimensions.

Pockets 534 and 536 are better illustrated in FIG. 22B which is a cutaway view of device 502. Between pockets 534 and 536 is a liquid seal 538 to protect electronics 510 from fluid that may leak from conduit 512 or in the event that reservoir 506 or actuator assembly 508 becomes ruptured. Also included are electrical leads 540 that couple electronics in pocket 536 to the actuator assembly 508 in pocket 534 and pass through seal 538.

Device 502 may also include a fluid fill port 513 for filling reservoir 506 with fluid. Alternatively reservoir 506 may be filled via fluid conduit 512. In a preferred embodiment, fluid fill port 513 or fluid conduit 512 are configured to enable reservoir 506 to be filled in a facility that is separate from the factory within which device 502 is manufactured.

FIG. 22C depicts a cross section of device 502 taken through section AA' of FIG. 22A. Arranged along depth axis Z from top to bottom are top or upper support 542, actuator assembly 508, collapsible reservoir 506, and lower support 544. Upper support 542 and lower support 544 are rigidly or fixedly positioned with respect to each other such that expansion of actuator assembly 508 is constrained to squeeze collapsible reservoir 506. In one embodiment, upper support 542 and lower support 544 are formed integrally with outer housing 504. In a second embodiment upper support 542 and lower support 544 are formed a second integral part that is mounted within housing 504. As a third embodiment upper support 542 and lower support 544 are formed as separate parts that are mounted to housing 504. In all embodiments upper support 542 and lower support 544 are configured to be in a fixed relationship to facilitate a proper interaction of actuator assembly 508 and collapsible reservoir 506 to assure reliable dispensing of fluid from collapsible reservoir 506 in response to dimensional expansion of actuator assembly 508 along thickness axis Z.

Figure 23A:
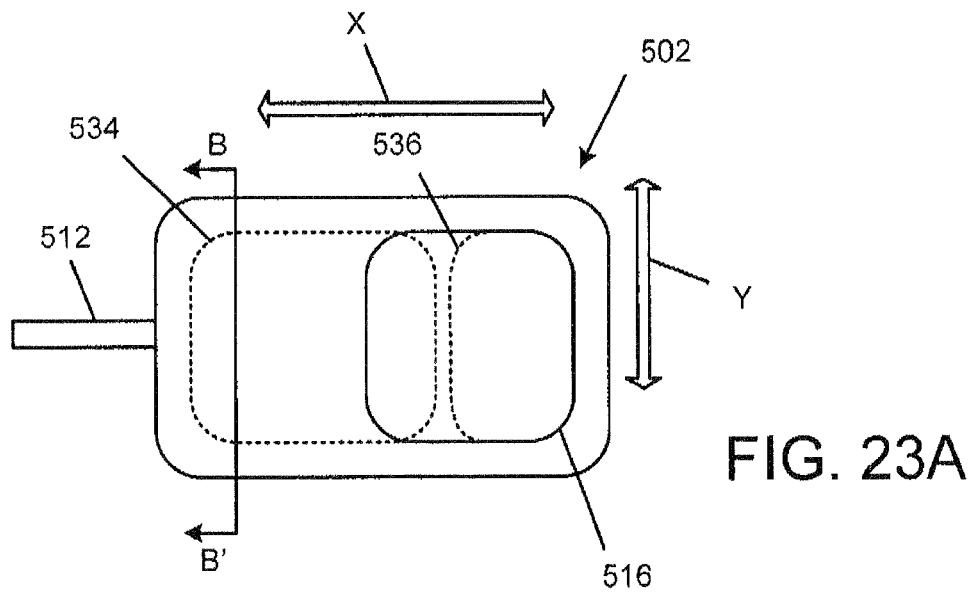
FIG. 23A depicts a plan view of a medication delivery device of the present invention.
Figure 23B:
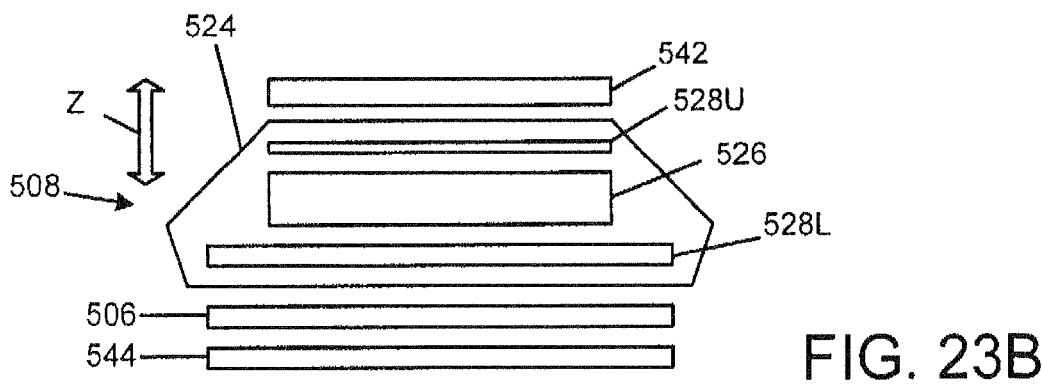
FIG. 23B depicts a cross-sectional view of a preferred embodiment of a portion of a medication delivery device of the present invention.
Figure 23C:
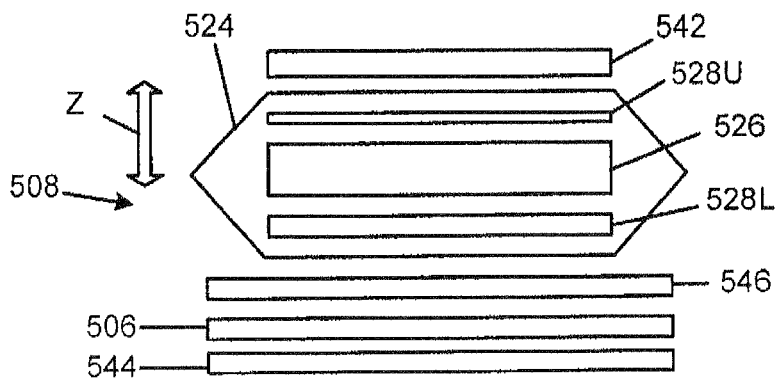
FIG. 23C depicts a cross-sectional view of an alternative embodiment of a portion of a medication delivery device of the present invention.

FIGS. 23A, 23B, and 23C provide a more detailed view of actuator assembly 508. FIG. 23A is a plan view of device 502 that is similar to FIG. 22A except that a cross section BB' is indicated taken through pocket 534. FIGS. 23B and 23C are cross sectional views taken through section BB' of FIG. 23C focusing on actuator assembly 508 and leaving out further details for simplicity.

FIG. 23B depicts a preferred embodiment of actuator assembly 508 having a film envelope or housing 524, upper electrode 528U, polymeric actuator 526, and lower electrode 528L. Upper electrode 528U is adjacent to upper support 542 and lower electrode 528L is adjacent to collapsible reservoir 506. In order to reduce a number of parts, the lower electrode 528L is configured to function as a piston plate to transfer an expansive force of polymeric actuator 526 to collapsible reservoir 506. In order to assure that collapsible reservoir can be fully compressed, the piston plate area is made to correspond to that of the fluid bag 506 and is relative thick and rigid. In order to maximize spatial efficiency in pocket 534 (to not make pocket 534 overly large relative to the size of reservoir 506) and to allow for expansion of film bag 524, the upper electrode 528U is sized smaller in area relative to piston plate/lower electrode 528L.

FIG. 23C depicts an alternative embodiment of actuator assembly 508 wherein piston plate 546 is a separate part rather than being the lower electrode 528L. In this alternative embodiment piston plate 546 is relatively rigid and sized with an area larger relative to upper electrode 528U. Piston plate 546 is sized to correspond to the size of collapsible reservoir 506 to maximize volumetric fluid delivery from device 502. Piston plate 546 is disposed between actuator assembly 508 and collapsible fluid reservoir 506.

In the embodiments depicted in FIGS. 23A-C the actuator assembly 508 overlays the fluid bag 506 and each have lateral dimensions along primary lateral axis X and secondary lateral axis Y that correspond closely to the lateral dimensions of pocket 534 in order to maximize the a total fluid volume output of device 502 relative to the size of device 502. The actuator 508 and the bag 506 have relatively thin dimensions along depth axis Z in order to minimize overall depth of device 502 to maximize patient comfort.

In both illustrated embodiments, upper electrode 528U is adjacent to upper support 542. Lower electrode/piston plate 528L or piston plate 546 is adjacent to collapsible reservoir 506. Collapsible reservoir 506 is adjacent to lower support 544.

Figure 24A:
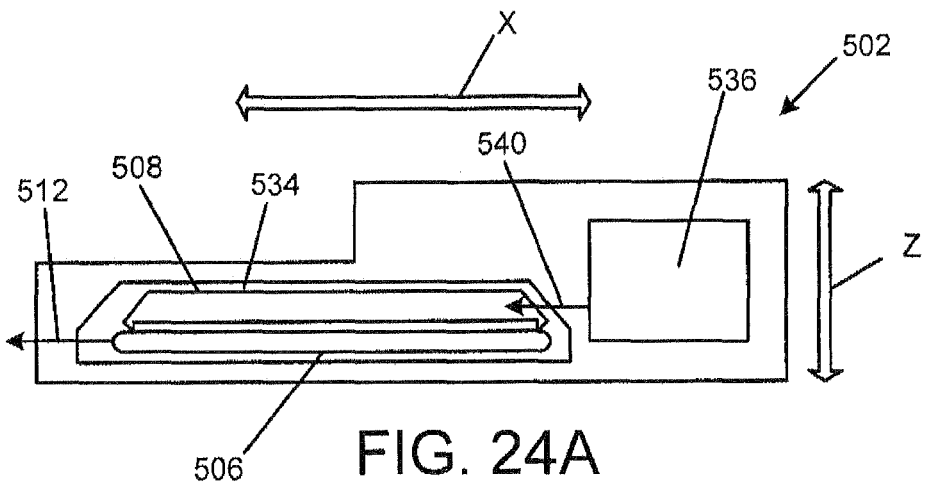
FIG. 24A depicts a cross-sectional view of a medication delivery device of the present invention.
Figure 24B:
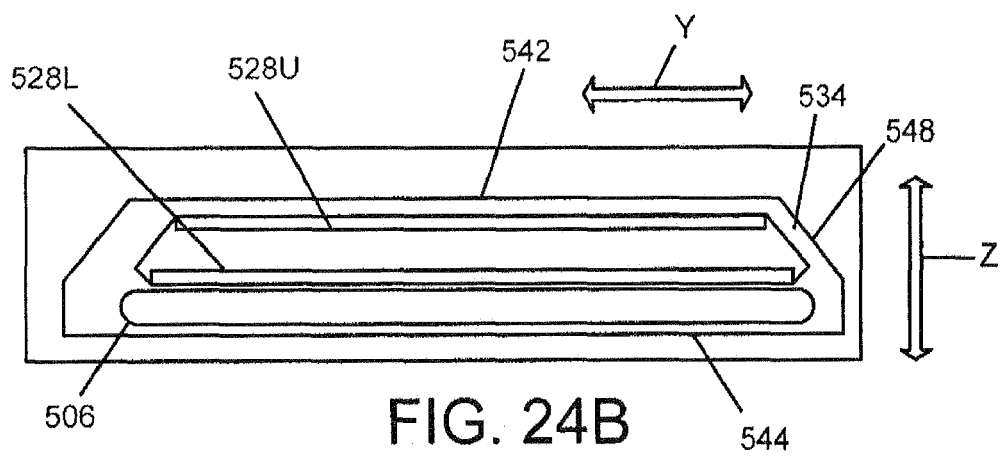
FIG. 24B depicts a cross sectional view of a preferred embodiment of an actuator/reservoir pocket.
Figure 24C:
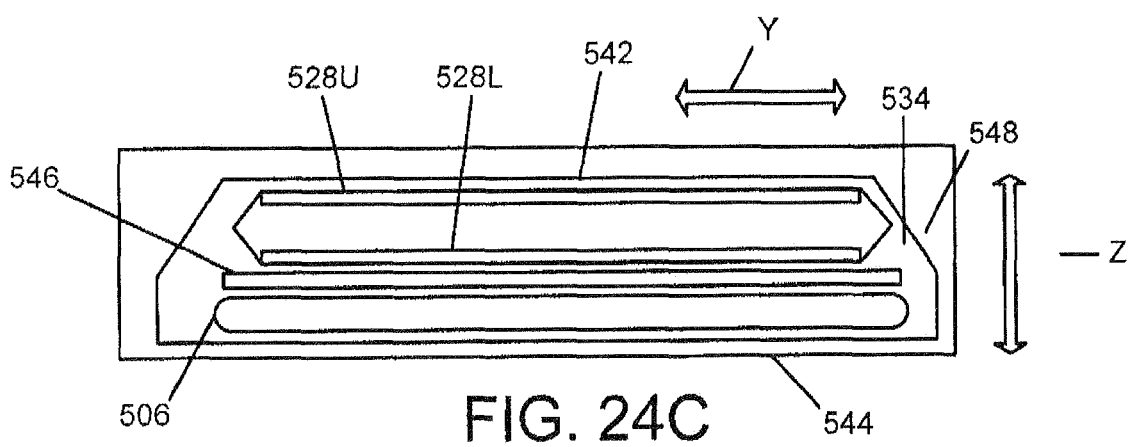
FIG. 24C depicts a cross-sectional view of an alternative embodiment of an actuator/reservoir pocket.

FIGS. 24A-C depict an exemplary embodiment of device 502 with emphasis on pockets 534 and 536. FIG. 24A is a cross sectional view taken through AA' of FIG. 22A illustrating pocket 534 and pocket 536. Pocket 534 contains actuator assembly 508 overlaying collapsible reservoir 506. Pocket 536 contains electronics 510 that are coupled to actuator 506 via leads 540. As can be seen, disposing actuator/reservoir pocket 534 and electronics pocket 536 along primary or major lateral axis X minimizes the dimension of device 502 along depth axis Z. The depth axis of a patient-worn device is the largest dimensionally-based source of discomfort for wearing such a device. The device of the present invention breaks new ground in terms of patient comfort relative to volume of medication delivered.

The reservoir/actuator pocket 534 is approximately square looking upon the lateral axes X and Y. This maximizes volumetric efficiency of the reservoir actuator pocket 534 in terms of volume of fluid delivered relative to size of device 502. Leading to the patient is a conduit 512 that, in an exemplary embodiment, exits pocket 543 on a side that opposes the electronics 510 relative to axis X. In addition, the electrical lead through 540 is on an opposing side of actuator pocket 534 relative to conduit 512 and relative to axis X.

FIG. 24B depicts a cross section of a preferred embodiment of pocket 534 taken through section BB' of FIG. 24A. In this preferred embodiment, lower electrode 528L is also a piston plate and has an area corresponding to that of collapsible reservoir 506. Upper electrode 528U has a smaller area relative to lower electrode 528L. Pocket 534 includes a tapered chamfered upper wall 548 that corresponds to the asymmetry between upper electrode 528U and lower electrode/piston plate 528L. An upper portion of pocket 534 provides upper support 542 and is adjacent to the upper electrode 528U of actuator assembly 508. A lower portion of pocket 534 provides lower support 544 and is adjacent to collapsible fluid reservoir 506.

FIG. 24C depicts an alternative embodiment of pocket 534 taken through section BB' of FIG. 23A. In this alternative embodiment electrodes 528U and 528L may be approximately the same size. A separate piston plate 546 is disposed between and adjacent to collapsible fluid reservoir 506 and actuator assembly 508. Piston plate 546 has an area that corresponds to that of collapsible fluid reservoir 506 to maximize delivery of fluid from reservoir 506. The area of piston plate 546 is relatively larger than the area of upper electrode 528U.

Figure 25:
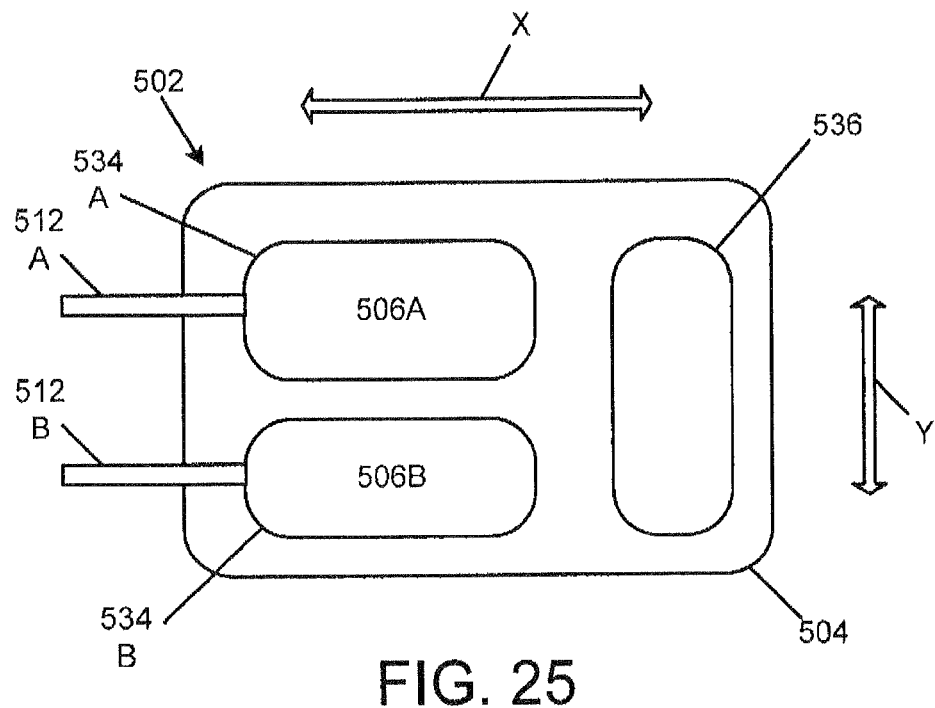
FIG. 25 depicts an alternative embodiment of a medication delivery device having more than one actuator/reservoir pocket.

FIG. 25 depicts an alternative embodiment of device 502 in plan cutaway view. FIG. 25 depicts a device 502 deploying two reservoir/actuator pockets 534A and 534B for dispensing two different fluids to a patient. Pocket 534A contains an actuator 508A overlaying a collapsible reservoir 506A containing a first fluid. Pocket 534B contains an actuator (not shown) overlaying a collapsible reservoir 506B containing a second fluid that is different than the first fluid. Fluids from bags 506A and 506B exit to the patient through fluid conduits 512A and 512B respectively. Fluid conduits 512A and 512B may combine to mix fluids prior to dispensing to the patient, or they may remain unmixed in individual conduits. Structures of the actuators, collapsible bags, and other features therein may be similar to those discussed with respect to FIGS. 21, 22C, 23B or 23C, and 24A or 24C.

Figure 26:
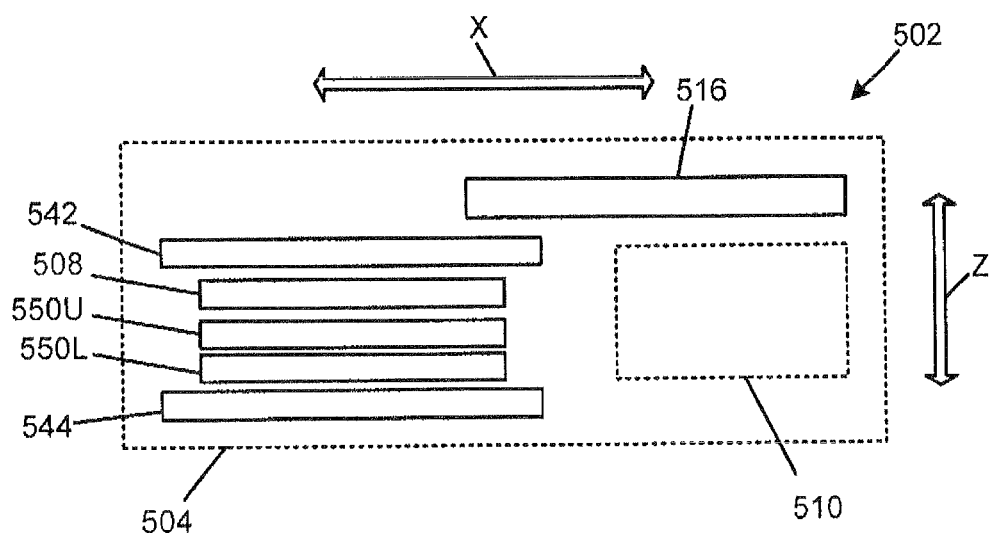
FIG. 26 depicts an alternative embodiment of a medication delivery device having more than one collapsible reservoir in an actuator/reservoir pocket.

FIG. 26 depicts an alternative embodiment of device 502 in cross section form taken through AA' of FIG. 22A. This alternative embodiment of device 502 deploys two fluid bags including a first fluid bag 550U overlaying a second fluid bag 550L. As actuator 526 expands, it compresses both fluid bags 550U and 550L simultaneously. Other elements such as housing 504, upper support 542, and lower support 544 are similar to those discussed with respect to FIG. 22C.

Figure 27:
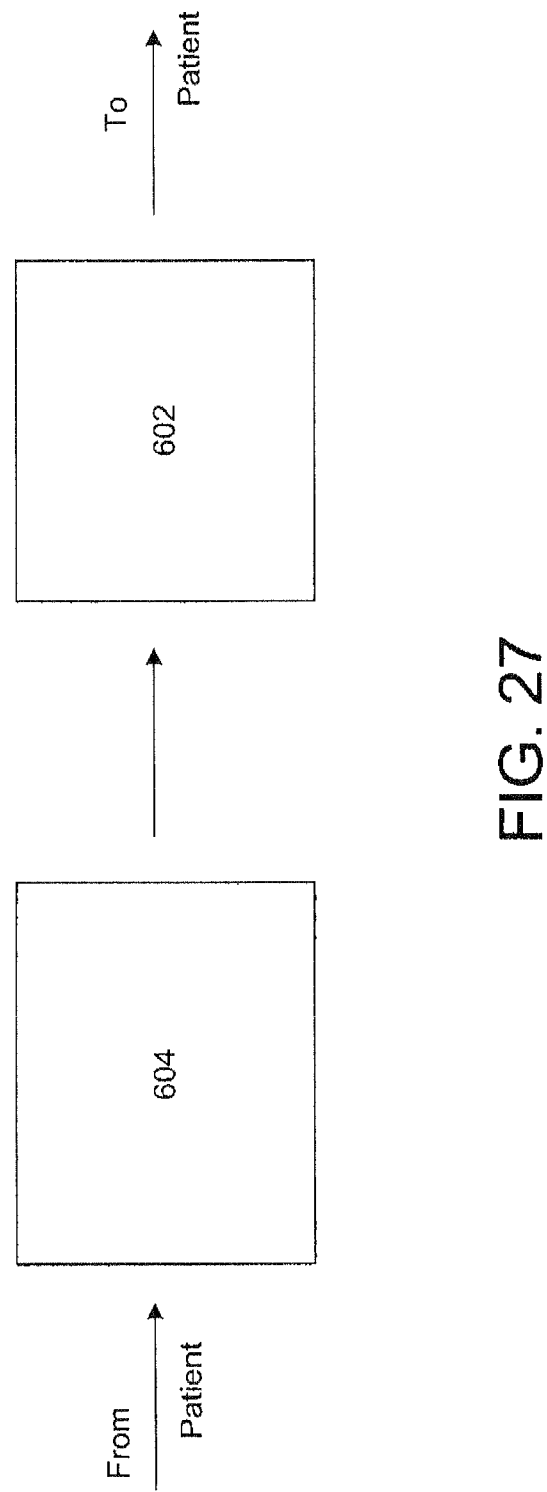
FIG. 27 is a block diagram depicting yet another alternative embodiment of the invention.

FIG. 27 illustrates yet another embodiment of the present invention. In this alternative embodiment, a liquid delivery device 602 as described above is paired with a patient monitoring device 604, such as a pulse oximeter, a blood $CO_2$ sensor, a respiration rate sensor, a blood pressure monitor, a glucose monitor, or the like, with feedback to the liquid delivery device controller, to adjust or stop the pump, or signal an alarm if the patient is showing signs of overmedication. The feedback also could be used to adjust the pump to deliver additional medication if the patient is showing signs of undermedication.

Other embodiments can be envisioned with other arrangements and configurations of fluid bags and actuators. The scope of the present invention is not intended to be limited except as recited in the claims.

What is claimed is:

1. A low profile medication delivery device comprising:
a chassis having a first dimension X, a second dimension Y orthogonal to the first dimension X, and a third dimension Z orthogonal to both first dimension X and second dimension Y, wherein the first dimension X and the second dimension X form a plane, and wherein the chassis has a first pocket and a second pocket;
an actuator assembly overlaying a plurality of collapsible reservoirs disposed within the first pocket; and
electronics disposed within the second pocket and coupled to the actuator assembly, the actuator assembly being configured to separately control expansion and compression of each collapsible reservoir in response to current being passed through the actuator assembly.

2. The low profile medication delivery device of claim 1, wherein the actuator assembly includes an upper electrode, a lower electrode, and a polymeric actuator between the upper electrode and the lower electrode; and wherein the actuator assembly optionally further includes:
a sealed flexible outer housing surrounding the upper electrode, the lower electrode, and the polymeric actuator; and
an electrolyte solution within the housing and in contact with the polymeric actuator, wherein the polymeric actuator is configured to expand in response to pH changes in the electrolyte solution induced by the current, wherein one of the electrodes preferably is surrounded, at least in part, by a porous separator membrane that facilitates modulation of the pH via charges separation.

3. The low profile medication delivery device of claim 1, further comprising:
an upper support adjacent to the upper electrode; and
a lower support adjacent the collapsible reservoir, wherein the lower electrode is adjacent to the collapsible reservoir and is configured to function as a piston plate that compresses the collapsible reservoir between the lower support and the lower electrode as the polymeric actuator expands.

4. The low profile medication delivery device of claim 1, further comprising:
an upper support adjacent to the upper electrode;
a lower support adjacent the plurality of collapsible reservoirs; and
a piston plate disposed between the lower electrode and the plurality of collapsible reservoirs.

5. The low profile medication delivery device of claim 1, further comprising:

wherein the chassis has a third pocket, and further comprising a second actuator assembly overlaying a second collapsible reservoir disposed within the third pocket.

6. The low profile medication delivery device of claim 1, further comprising:
wherein at least two but not all of the collapsible reservoirs are configured to be simultaneously pressurized by the actuator when current is passed through the actuator.

7. The low profile medication delivery device of claim 1, further comprising:
wherein the chassis has a length defined along a primary lateral axis, a width defined along a secondary lateral axis, and a depth defined along a depth axis, the chassis having a first pocket and a second pocket arranged and separated along the primary lateral axis to minimize the depth, the length greater than the width, the width greater than the depth;
the actuator assembly overlaying the plurality of collapsible reservoirs disposed within the first pocket; and
electrical leads coupling the electronics to the actuator assembly.

8. The low profile medication delivery device of claim 7, further comprising:
wherein the actuator assembly expands along the depth axis in response to charge passed from the electronics to the actuator;
the actuator assembly includes a polymeric actuator that expands in response to pH changes within the actuator assembly, and the electronics are configured to deliver current to the actuator assembly that modulates the pH; and
the primary lateral axis, the secondary lateral axis, and the depth axis are mutually perpendicular.

9. The low profile medication delivery device of claim 1, further comprising:
further comprising:
a lower support;
an upper support fixedly coupled to the lower support;
a collapsible fluid reservoir positioned adjacent to the lower support;
an actuator assembly positioned between the collapsible fluid reservoir and the upper support, the actuator assembly including:
an upper electrode proximate the upper support; and
a polymeric actuator positioned adjacent to the upper electrode; and
a piston plate positioned between the polymeric actuator and the collapsible fluid reservoir.

10. The low profile medication delivery device of claim 9, further comprising:
wherein the polymeric actuator is configured to change dimensionally in response to pH changes within the actuator assembly;
the piston plate is a lower electrode within the actuator assembly;
the actuator assembly includes a lower electrode that is proximate to the piston plate; and
the upper electrode has a first area, the piston plate has a second area that is larger than the first area to maximize volumetric efficiency of the low profile medication delivery apparatus.

11. The low profile medication delivery device of claim 10, further comprising:
(v) further comprising a housing having mutually orthogonal axes including a major lateral axis having a first dimension, a minor lateral axis having a second dimension, and a depth axis having a third dimension, the housing enclosing two pockets that are arranged along the major lateral axis including a first pocket and a second pocket, the actuator assembly overlaying the plurality of collapsible reservoirs within the first pocket, the depth axis less than either the first dimension or the second dimension, wherein the second pocket optionally contains electronics coupled to the actuator assembly and configured to deliver current to the actuator assembly, the actuator assembly configured to increase a dimension in the depth axis and to compress the plurality of collapsible reservoirs in response to the current.

12. A low profile medication delivery device comprising:
a chassis having a first dimension X, a second dimension Y orthogonal to the first dimension X, and a third dimension Z orthogonal to both first dimension X and second dimension Y, wherein the first dimension X and the second dimension Y form a plane, and wherein the chassis has a first pocket and a second pocket;
an actuator assembly including a rigid electrode which functions as a rigid platen overlaying a collapsible reservoir disposed within the first pocket; and
electronics disposed within the second pocket and coupled to the actuator assembly, the actuator assembly being configured to control expansion and compression of the collapsible reservoir in response to current being passed through the actuator assembly.

13. The low profile medication delivery device of claim 12, wherein the actuator assembly includes an upper electrode, a lower electrode, and a polymeric actuator between the upper electrode and the lower electrode; and wherein the actuator assembly optionally further includes:
a sealed flexible outer housing surrounding the upper electrode, the lower electrode, and the polymeric actuator; and
an electrolyte solution within the housing and in contact with the polymeric actuator, wherein the polymeric actuator is configured to expand in response to pH changes in the electrolyte solution induced by the current, wherein one of the electrodes preferably is surrounded, at least in part, by a porous separator membrane that facilitates modulation of the pH via charges separation.

14. The low profile medication delivery device of claim 12, further comprising:
an upper support adjacent to the upper electrode; and
a lower support adjacent the collapsible reservoir, wherein the lower electrode is adjacent to the collapsible reservoir and is configured to function as a piston plate that compresses the collapsible reservoir between the lower support and the lower electrode as the polymeric actuator expands.

15. The low profile medication delivery device of claim 12, further comprising:
an upper support adjacent to the upper electrode;
a lower support adjacent the collapsible reservoir; and
a piston plate disposed between the lower electrode and the collapsible reservoir.

16. The low profile medication delivery device of claim 12, further comprising:
wherein the chassis has a third pocket, and further comprising a second actuator assembly overlaying a second collapsible reservoir disposed within the third pocket.

17. The low profile medication delivery device of claim 12, further comprising:
wherein at least two collapsible reservoirs configured to be simultaneously pressurized by the actuator when current is passed through the actuator.

18. The low profile medication delivery device of claim 12, further comprising:
- wherein the chassis has a length defined along a primary lateral axis, a width defined along a secondary lateral axis, and a depth defined along a depth axis, the chassis having a first pocket and a second pocket arranged and separated along the primary lateral axis to minimize the depth, the length greater than the width, the width greater than the depth;
- the actuator assembly overlaying collapsible reservoir disposed within the first pocket; and
- electrical leads coupling the electronics to the actuator assembly.

19. The low profile medication delivery device of claim 18, further comprising:
- wherein the actuator assembly expands along the depth axis in response to charge passed from the electronics to the actuator;
- the actuator assembly includes a polymeric actuator that expands in response to pH changes within the actuator assembly, and the electronics are configured to deliver current to the actuator assembly that modulates the pH; and the primary lateral axis, the secondary lateral axis, and the depth axis are mutually perpendicular.

20. The low profile medication delivery device of claim 12, further comprising:
- further comprising:
- a lower support;
- an upper support fixedly coupled to the lower support;
- a collapsible fluid reservoir positioned adjacent to the lower support;
- an actuator assembly positioned between the collapsible fluid reservoir and the upper support, the actuator assembly including:
- an upper electrode proximate the upper support; and
- a polymeric actuator positioned adjacent to the upper electrode; and
- a piston plate positioned between the polymeric actuator and the collapsible fluid reservoir.

21. The low profile medication delivery device of claim 20, further comprising:
- wherein the polymeric actuator is configured to change dimensionally in response to pH changes within the actuator assembly;
- the piston plate is a lower electrode within the actuator assembly;
- the actuator assembly includes a lower electrode that is proximate to the piston plate; and
- the upper electrode has a first area, the piston plate has a second area that is larger than the first area to maximize volumetric efficiency of the low profile medication delivery apparatus.

22. The low profile medication delivery device of claim 21, further comprising:
- (v) further comprising a housing having mutually orthogonal axes including a major lateral axis having a first dimension, a minor lateral axis having a second dimension, and a depth axis having a third dimension, the housing enclosing two pockets that are arranged along the major lateral axis including a first pocket and a second pocket, the actuator assembly overlaying the collapsible reservoir within the first pocket, the depth axis less than either the first dimension or the second dimension, wherein the second pocket optionally contains electronics coupled to the actuator assembly and configured to deliver current to the actuator assembly, the actuator assembly configured to increase a dimension in the depth axis and to compress the collapsible reservoir in response to the current.

* * * * *